US011253188B2

United States Patent
Tal Fass

(10) Patent No.: US 11,253,188 B2
(45) Date of Patent: Feb. 22, 2022

(54) MEANS AND METHODS FOR PERSONALIZED BEHAVIORAL HEALTH ASSESSMENT SYSTEM AND TREATMENT

(71) Applicant: NTW LTD., Ramat Hasharon (IL)

(72) Inventor: Michal Tal Fass, Ramat Hasharon (IL)

(73) Assignee: NTW LTD., Ramat Hasharon (IL)

( * ) Notice: Subject to any disclaimer, the term of this patent is extended or adjusted under 35 U.S.C. 154(b) by 0 days.

(21) Appl. No.: 17/261,833

(22) PCT Filed: Jul. 22, 2019

(86) PCT No.: PCT/IL2019/050829
§ 371 (c)(1),
(2) Date: Jan. 20, 2021

(87) PCT Pub. No.: WO2020/021542
PCT Pub. Date: Jan. 30, 2020

(65) Prior Publication Data
US 2021/0251554 A1 Aug. 19, 2021

Related U.S. Application Data

(60) Provisional application No. 62/701,785, filed on Jul. 22, 2018.

(51) Int. Cl.
*A61B 5/375* (2021.01)
*G16H 20/70* (2018.01)
(Continued)

(52) U.S. Cl.
CPC .............. *A61B 5/375* (2021.01); *A61B 5/165* (2013.01); *A61B 5/4094* (2013.01);
(Continued)

(58) Field of Classification Search
CPC ......... A61B 5/165; A61B 5/167; A61B 5/375; A61B 5/4806; A61B 5/4094; A61N 1/36025; G16H 20/70
See application file for complete search history.

(56) References Cited

U.S. PATENT DOCUMENTS 8,380,316 B2  2/2013  Hagedorn et al.
2003/0233250 A1*  12/2003  Joffe .................. G16H 15/00
                                                            705/2
(Continued)

FOREIGN PATENT DOCUMENTS

CN       106344009 A     1/2017
WO       2011051955 A2   5/2011

OTHER PUBLICATIONS

PCT Search Report for International Application No. PCT/IL2019/050829 dated Nov. 3, 2019, 4 pp.
(Continued)

*Primary Examiner* — Thaddeus B Cox
(74) *Attorney, Agent, or Firm* — The Roy Gross Law Firm, LLC; Roy Gross

(57) ABSTRACT

The invention presented personalized biofeedback computerized system, an End-to-End eHealth smart platform for analysis, diagnosis and therapy of types of behavioral disorders. The system comprises a Captive Portal (CP) data input for initial input data and for continuous input data, a database comprising data, a Computer Processing Manager (CPM) for processing the patient data and the database, a Graphical User Interface (GUI) for interfacing with a user, and an Electroencephalography (EEG) or hemoencephalography (HEG) cap for stimulating predetermined areas in the brain, wherein the CPM is interconnected to the CPP, the database and the GUI, the CPM provides instructions for cranial electrode mediated stimulation to the areas in the brain according to a predetermined patient data dependent (Continued)

protocol, and the database provides external data. A preferred embodiment of the invention is a multilayered biofeedbacking system.

19 Claims, 19 Drawing Sheets

(51) Int. Cl.
*A61B 5/16* (2006.01)
*A61N 1/36* (2006.01)
*G16H 20/40* (2018.01)
*A61B 5/00* (2006.01)

(52) U.S. Cl.
CPC ........ *A61B 5/4806* (2013.01); *A61N 1/36025* (2013.01); *G16H 20/40* (2018.01); *G16H 20/70* (2018.01)

(56) References Cited

U.S. PATENT DOCUMENTS

| 2014/0223462 A1* | 8/2014 | Aimone | G16H 40/67 |
| | | | 725/10 |
| 2017/0134946 A1* | 5/2017 | Kang | H04L 63/083 |

OTHER PUBLICATIONS

Written Opinion for International Application No. PCT/IL2019/050829 dated Nov. 3, 2019, 4 pp.
International Preliminary Report on Patentability for International Application No. PCT/IL2019/050829 dated Dec. 28, 2020, 32 pp.

* cited by examiner

MEANS AND METHODS FOR PERSONALIZED BEHAVIORAL HEALTH ASSESSMENT SYSTEM AND TREATMENT

CROSS REFERENCE TO RELATED APPLICATIONS

This application is a National Phase of PCT Patent Application No. PCT/IL2019/050829 having International filing date of Jul. 22, 2019, which claims the benefit of priority of U.S. Provisional Patent Application No. 62/701,785, filed Jul. 22, 2018, the contents of which are all incorporated herein by reference in their entirety.

FIELD OF THE INVENTION

The invention presented means and methods for personalized behavioral health assessment system and treatment.

BACKGROUND OF THE INVENTION

To date, subjective questionnaires or sophisticated objective physiological scans have been used to assess emotional or behavioral cognitive disorders Emotional or behavioral cognitive disorders such as eating disorders, obesity, uncontrolled eating and unbalanced eating, ADHD, addictions, eating behaviors, depression, anxiety, autism, as well pain, fertility fibromyalgia, sleep disorders adversely affect individuals both medically and psychologically, leading to reduced life expectancy and poor quality of life.

Despite the clear evidence of clinical significance and despite availability of evidence-based, effective treatments, research has shown a paradox of elevated health services use and, yet, infrequent treatment. Moreover, While there exists a number of treatments for these emotional or behavioral cognitive disorders, many patients do not respond favorably to current behavioral, medical or surgical management.

It is hence evident that there is a high unmet treatment need and need for cost-effective and available simple means and interventions method to assist community members, health professionals and treatment services to recognize and diagnose these disorders efficiently and rapidly as well as providing appropriate and timely treatment.

Furthermore, there is unmet need for encouragement and motivation of the users and patients toward medical adherence and compliance for the available treatments.

SUMMARY OF THE INVENTION

It is hence an object of the invention to disclose a bio-feedbacking system characterized by
  a. a user-derived, internal-data source, captive portal data input (CP); said data is selected from a group consisting of data comprising basic input data, passive continuous input data and active input data;
  b. a external-data source database;
  c. a graphical user interface (GUI);
  d. an EEG wearable device configured for both sensing and for stimulating defined area of patient's brain; and
  e. a computer processing manager (CPM) for processing both said internal data and external data, interconnected with said CP, said database and said GUI; said CPM is configured to instruct cranial electrode mediated electro-stimulation to stimulate said area of patient's brain according to said patient-data driven stimulating-protocol.

It is hence an object of the invention to disclose a bio-feedbacking system characterized by
  a. a user-derived, internal-data source, captive portal data input (CP); said data is selected from a group consisting of data comprising basic input data, passive continuous input data and active input data;
  b. an external-data source database;
  c. a graphical user interface (GUI);
  d. a HEG wearable device configured for both sensing and for stimulating defined area of patient's brain; and
  e. a computer processing manager (CPM) for processing both said internal data and external data, interconnected with said CP, said database and said GUI; said CPM is configured to instruct cranial HEG electrode to stimulate said area of patient's brain according to said patient-data driven protocol.

It is hence an object of the invention to disclose a bio-feedbacking system characterized by
  a. a user-derived, internal-data source, captive portal data input (CP); said data is selected from a group consisting of data comprising basic input data, passive continuous input data and active input data;
  b. an external-data source database;
  c. a graphical user interface (GUI);
  d. an EEG or HEG wearable device configured for both sensing and stimulating defined area of patient's brain; and
  e. a computer processing manager (CPM) for processing both said internal data and external data, interconnected with said CP, said database and said GUI; said CPM is configured to instruct cranial EEG or HEG electrode to stimulate said area of patient's brain according to said patient-data driven protocol.

It is hence an object of the invention to disclose a bio-feedbacking system
useful for the treatment of at least one of eating disorders, obesity, uncontrolled or unbalanced eating, diabetes, sleep disorders, sleep apnea and uncontrolled behaviors, characterized by:
  a. a user-derived, internal-data source, captive portal data input (CP); said data is selected from a group consisting of data comprising basic input data, passive continuous input data and active input data;
  b. a external-data source database;
  c. a graphical user interface (GUI);
  d. an EEG wearable device configured for both sensing and for stimulating defined area of patient's brain; and
  e. a computer processing manager (CPM) for processing both said internal data and external data, interconnected with said CP, said database and said GUI; said CPM is configured to instruct cranial electrode mediated electro-stimulation to stimulate said area of patient's brain according to said patient-data driven stimulating-protocol.

1. The system of claim 4, wherein said system is an adjunctive therapy for at least one of therapies for eating disorders, uncontrolled or unbalanced eating, diabetes, sleep disorders, sleep apnea and uncontrolled behaviors.

It is hence an object of the invention to disclose a multilayered bio-feedbacking system comprising:
  a. a user derived module, comprising an internal-data source captive portal data input (CP); said data is selected from a group consisting of input data, passive continuous input data and active input data;
  b. an external module comprising database derived from user's logged behavior;

c. a wearable module, intercommunicable with said user derived module, comprising:
  i. at least one first sensor and at least one second sensor; said at least one first sensor is configured to log at least one first user's behavior, said at least one first behavior is characterized by a series of n events, n is an integer number being greater than or equals 1; and, said at least one second sensor is configured to log at least one second user's behavior, said at least one second behavior is characterized by a series of m events, m is an integer number being greater than or equals 1; and,
  ii. at least one first and at least one second stimulation modules for stimulating a response for said at least one first and second user's behaviors, respectively, said response is stimulated in connection with said n' and m' events; n' and m', respectively, are an integer numbers, each of which is being greater than or equals 1; each of which of said at least one first and second stimulation modules are in connection with either or both
    (1) one or more signal inducers configured for a conscious alert; and
    (2) one or more signal inducers configured for either a conscious or a subconscious stimulation at one or more locations of user's brain;
d. a multilayered supervising processor structured with at least one first stimulus-respond reflex lower-layer and at least one second processing-supervising reflex upper-layer; said processor comprises a user driven behaviors-hierarchy optimizer configuring for storing and processing parameters derived from user's behavior, weighing and defining hierarchy of the same, and either offline or online providing critical go/no-go values and allowable measures' range for said parameters; said processor is configured for operating as follows:
  i. in said lower reflex layer, and for both at least one first and at least one second behaviors, by means of at least a portion of said sensors intercommunicated with said wearable module, detecting said n and m events and defining the same as $n^{th}$ or $m^{th}$ stimulus;
  ii. by communicating with said behaviors-hierarchy optimizer, correlating said stimulus with at least one parameter derived from user's at least one first behavior, weighing said parameter, and subsequently defining a response for said at least one first behavioral stimulus;
  iii. in said upper reflex-like layer, and for both at least one first and at least one second behaviors, weighting said n and m events; detecting prevalence and magnitude of said events, processing the same, and supervising said lower reflex-like layer such that one of the following is being held true:
    (1) decreasing response for stimuli of said first behavior if both hierarchy of second behavior is higher than hierarchy of first behavior prevalence and magnitude of said first behavior is lower than prevalence and magnitude of said second behavior;
    (2) decreasing response for stimuli of said first behavior if both hierarchy of second behavior is higher than hierarchy of first behavior prevalence, magnitude of said first behavior is higher than prevalence and magnitude of said second behavior; and at least one parameter derived from user's first behavior is lower than critical go/no-go, and values of said at least one said pre-determined parameter are within allowable measures' range;
    (3) allowing response for both stimuli of said of said first behavior and stimuli of said second behavior, if both hierarchy of second behavior is higher than hierarchy of first behavior, prevalence and magnitude of said first behavior is lower than prevalence and magnitude of said second behavior, and at least one parameter derived from user's first behavior is higher than critical go/no-go, and values of said at least one said pre-determined parameter are not within allowable measures' range;
    (4) allowing response for both stimuli of said of said first behavior and stimuli of said second behavior, if both hierarchy of second behavior is higher than hierarchy of first behavior, prevalence and magnitude of said first behavior is higher than prevalence and magnitude of said second behavior, and at least one parameter derived from user's first behavior is higher than critical go/no-go, and values of said at least one said pre-determined parameter are not within allowable measures' range;

It is hence another object of the invention to disclose the multilayered bio-feedbacking system of any of the above claims, wherein said parameters derived from user's behavior comprise data driven from user's behavior; user's location at time, user's adjacent mapping and user's close and remote environment and coordinates thereof, user's scheduled activity, user's physical, physiological, biological, chemical and emotional quantifiably parameters, and hierarchy thereof; distance travelled measured by an accelerometer, velocity, heart rate, blood pressure, body temperature, sleeping time, duration of phone calls, numbers of outgoing and incoming calls and text messages, identification of calls and callers, number of calls, length of calls, number of unique calls, number and duration of visits in restaurants, and fast food sites, sport's sites including swimming pools, gym, camera photos, location, acquisitions, electrical activity of the brain, mood parameters, including variability and frequency of mood change, increased blood pressure, prolonged skin problems, extreme change in appetite, excess gas, frequent dizziness, gastric ulcer, myocardial infarction, inability to work, nightmares, feeling incompetent in all areas, desire to escape everything, apathy, depression or prolonged anger, excessive tiredness, thinking/talking over and over about the same topic, irritability for no apparent reason, daily distress/anxiety, emotional hypersensitivity, loss of sense of humor, cold hands and/or feet, dry mouth, stomach pain, increased sweating, muscle tension, tightening of the jaw/teeth grinding, transient diarrhea, insomnia, tachycardia (increased heart rate) hyperventilation (increased respiratory rate), sudden or transient increased blood pressure, change in appetite, surge of motivation, sudden enthusiasm, sudden urge to start new projects, memory problems, general malaise without specific cause, tingling of the extremities, feeling of constant physical strain, change in appetite, skin problems, increased blood pressure, constant tiredness, gastritis/gastric ulcer, dizziness/feeling as if floating, excessive emotional sensitivity, self-doubt, constant thought about the same topic, constant irritability, decreased libido, frequent diarrhea, sexual difficulties, insomnia, nausea, tics and any combination thereof.

It is hence another object of the invention to disclose the system of any of the above claims, wherein said captive portal is configured to collect and store said subject's data input.

It is hence another object of the invention to disclose the system of any of the above claims, wherein said system is either stationary or mobile.

It is hence another object of the invention to disclose the system of any of the above claims, wherein said CP comprises an algorithm configured to weigh the results of said data input, with said data of said database.

It is hence another object of the invention to disclose the system of any of the above claims, wherein said instructions for electrostimulation comprises at least one of the group consisting of a wearable neurofeedback (NF) system and a wearable neurofeedback system using virtual reality (VR)

It is hence another object of the invention to disclose the neurofeedback of any of the above claims, wherein said system comprises at least one EEG electrode configured to stimulate at least one brain area.

It is hence another object of the invention to disclose the system of any of the above claims, wherein said system mammalian subject is a human patient.

It is hence another object of the invention to disclose the system of any of the above claims, wherein said system is useful for treating eating disorders.

It is hence another object of the invention to disclose the system of any of the above claims, wherein said system is useful for increasing at least one selected from the group consisting of ability to organize, persistence, temptation resistance, devoting, awareness of the need to change, abilities to persist, planning, optimism, being essential, being organized, being aware of quality, being attentive to hunger, managing to be particular, motivating to be particular, readiness for treatment, sleeping quality, faith in own ability, and any combination thereof.

It is hence another object of the invention to disclose the system of any of the above claims, wherein said system is useful for treating at least one condition selected from emotional eating, anxiety, impulsiveness, frustration of food, urge to eat, physical problems, and any combination thereof.

It is hence another object of the invention to disclose the system of any of the above claims, wherein said system is useful for treating at least one of a group consisting of eating disorders, unbalanced eating, uncontrolled eating or obesity, ADHD, addictions, ADD, eating behaviors, depression, anxiety, autism, as well as eating accompanying diseases anxiety addictions, pain, sexuality and fertility, fibromyalgia performance, sleep disorders and any combination thereof.

It is hence another object of the invention to disclose the system of any of the above claims, said eating disorders are selected from a group consisting non-diagnosed eating disorders, unbalanced eating, uncontrolled eating, industrial eating, obesity, anorexia nervosa, bulimia nervosa, muscle dysmorphia, Binge Eating Disorder, Other Specified Feeding or Eating Disorder, atypical anorexia nervosa, atypical bulimia nervosa, Eating Disorders, disorders with symptoms similar to anorexia or bulimia that do not meet all diagnostic criteria for DSM disorders and any combination thereof It is hence another object of the invention to disclose the system of any of the above claims, wherein said human patient is selected from a group of patients not diagnosed with obesity, patient diagnosed with obesity, patient diagnosed with AD(H)D, patient not diagnosed with AD(H)D, patient diagnosed with eating disorders, and patient not diagnosed with eating disorders.

It is hence another object of the invention to disclose the CPM of any of the above claims, wherein said CPM further provides instructions for cannabinoid-based therapy adjunct to said cranial electrode mediated electro stimulation.

It is hence another object of the invention to disclose the system of any of the above claims, wherein eating disorders are selected from a group consisting of: Anorexia Nervosa, Bulimia Nervosa, Binge Eating Disorder (BED), Avoidant/Restrictive Food Intake Disorder (ARFID), obesity, unbalanced eating, selective eating, western industrial eating, orthorexia, excessive exercise and any combination thereof.

It is hence another object of the invention to disclose the system of any of the above claims, wherein Passive Continuous Input Data comprises at least one of said subject's parameters selected from EEG, HEG, QEEG distance travelled, velocity, heart rate, blood pressure, body temperature, sleeping time, duration of phone calls, number of outgoing and incoming calls and text messages, identification of phone calls and callers, length of calls, WhatsApp messages, Social networks' usage, visits in restaurants, visits in in fast food sites, visits in swimming pools, visits in gym, camera photos, location, acquisitions and any combination thereof.

It is hence another object of the invention to disclose the system of any of the above claims, wherein Passive Continuous Input Data is assembled by a device is selected from a group of an EEG, a camera, a mobile phone, a smartphone, a watch, a smart watch, a bracelet, a smart bracelet, a wristband, a smart wristband, a smart band and any combination thereof.

It is hence another object of the invention to disclose the system of any of the above claims, wherein Basic Input Data comprises personal details, said personal details are weight, body fat, height, age, BMI, body fat, muscle mass and gender.

It is hence another object of the invention to disclose the system of any of the above claims, wherein Active Input Data comprises at least one of a personal characterization questionnaire, an eating and diet preferences questionnaire, a "Health promoting questionnaire" and any combination thereof.

It is hence another object of the invention to disclose the system of any of the above claims, configured to repeat to collect said data following said treatment of said eating disorders at plurality of time points, to determine whether the subject is responsive; and to recommend the stimulation to be continued if the subject is responsive or to be discontinued is the subject is non responsive.

It is hence another object of the invention to disclose the system of any of the above claims, wherein said CP further configured to collect said data following said treatment of said eating disorders, at n time points, wherein n is an integer equal of higher than 2, comprising of first time point before start of said treatment of said eating disorders and a second time point at a later time over life of said mammalian subject; further wherein said CMP configured to provide instructions for cranial electrode mediated electro stimulation to said areas in the brain according to a predetermined patient data dependent protocol, and said database provides data related to eating disorders, and said stimulation be continued, if values of said mammalian subject's weight in said input data at second time point are lower than value at said first time point i.e. subject.

It is one object of the invention to disclose a method of bio-feedbacking, the method characterized by
  a. providing a user-derived, internal-data source, captive portal data input (CP); said data is selected from a group consisting of data comprising basic input data, passive continuous input data and active input data;
b. providing a external-data source database;
c. providing a graphical user interface (GUI);
d. providing an EEG wearable device configured for both sensing and for stimulating defined area of patient's brain; and
e. providing computer processing manager (CPM) for processing both said internal data and external data, interconnected with said CP, said database and said GUI; said CPM is configured to instruct cranial electrode mediated electro-stimulation to stimulate said area of patient's brain according to said patient-data driven stimulating-protocol.

It is one object of the invention to disclose a method of treating at least one of eating disorders, obesity, uncontrolled or unbalanced eating, diabetes, sleep disorders, sleep apnea and uncontrolled behaviors. The method characterized by:
a. providing a user-derived, internal-data source, captive portal data input (CP); said data is selected from a group consisting of data comprising basic input data, passive continuous input data and active input data;
b. providing a external-data source database;
c. providing a graphical user interface (GUI);
d. providing an EEG wearable device configured for both sensing and for stimulating defined area of patient's brain; and
e. providing a computer processing manager (CPM) for processing both said internal data and external data, interconnected with said CP, said database and said GUI; said CPM is configured to instruct cranial electrode mediated electro-stimulation to stimulate said area of patient's brain according to said patient-data driven stimulating-protocol.

It is one object of the invention to disclose a method of bio-feedbacking by means of a multilayered system, said method comprising:
a. providing a user derived module, comprising an internal-data source captive portal data input (CP); said data is selected from a group consisting of input data, passive continuous input data and active input data;
b. providing an external module comprising database derived from user's logged behavior;
c. providing a wearable module, intercommunicable with said user derived module, this family of steps comprising steps of
 i. providing at least one first sensor and at least one second sensor;
  said at least one first sensor is configured to log at least one first user's behavior,
  said at least one first behavior is characterized by a series of n events, n is an integer number being greater than or equals 1; and,
  said at least one second sensor is configured to log at least one second user's behavior, said at least one second behavior is characterized by a series of m events, m is an integer number being greater than or equals 1; and,
 ii. providing at least one first and at least one second stimulation modules for stimulating a response for said at least one first and second user's behaviors, respectively, said response is stimulated in connection with said n' and m' events; n' and m', respectively, are integer numbers, each of which is being greater than or equals 1; each of which of said at least one first and second stimulation modules are in connection with either or both
  (1) one or more signal inducers configured for a conscious alert; and
  (2) one or more signal inducers configured for either a conscious or a subconscious stimulation at one or more locations of user's brain;
d. providing a multilayered supervising processor structured with at least one first stimulus-respond reflex lower-layer and at least one second processing-supervising reflex upper-layer; said processor comprises a user driven behaviors-hierarchy optimizer configuring for storing and processing parameters derived from user's behavior, weighing and defining hierarchy of the same, and either offline or online providing critical go/no-go values and allowable measures' range for said parameters;
e. configuring said processor for operating as follows: in said lower reflex layer, and for both at least one first and at least one second behaviors, by means of at least a portion of said sensors intercommunicated with said wearable module, detecting said n and m events and defining the same as $n^{th}$ or $m^{th}$ stimulus; by communicating with said behaviors-hierarchy optimizer, correlating said stimulus with at least one parameter derived from user's at least one first behavior, weighting said parameter, and subsequently defining a response for said at least one first behavioral stimulus; in said upper reflex-like layer, and for both at least one first and at least one second behaviors, weighting said n and m events; detecting prevalence and magnitude of said events, processing the same, and
f. supervising said lower reflex-like layer such that one of the following is being held true:
 (1) decreasing response for stimuli of said first behavior if both hierarchy of second behavior is higher than hierarchy of first behavior prevalence and magnitude of said first behavior is lower than prevalence and magnitude of said second behavior;
 (2) decreasing response for stimuli of said first behavior if both hierarchy of second behavior is higher than hierarchy of first behavior prevalence, magnitude of said first behavior is higher than prevalence and magnitude of said second behavior; and at least one parameter derived from user's first behavior is lower than critical go/no-go, and values of said at least one said pre-determined parameter are within allowable measures' range;
 (3) allowing response for both stimuli of said of said first behavior and stimuli of said second behavior, if both hierarchy of second behavior is higher than hierarchy of first behavior, prevalence and magnitude of said first behavior is lower than prevalence and magnitude of said second behavior, and at least one parameter derived from user's first behavior is higher than critical go/no-go, and values of said at least one said pre-determined parameter are not within allowable measures' range;
 (4) allowing response for both stimuli of said of said first behavior and stimuli of said second behavior, if both hierarchy of second behavior is higher than hierarchy of first behavior, prevalence and magnitude of said first behavior is higher than prevalence and magnitude of said second behavior, and at least one parameter derived from user's first behavior is higher than critical go/no-go, and values of said at least one said pre-determined parameter are not within allowable measures' range.

2. It is one object of the invention to disclose a method of bio-feedbacking as defined in any of the above claims, wherein said parameters derived from user's behavior comprise data driven from user's behavior; user's location at time, user's adjacent mapping and user's close and remote environment and coordinates thereof, user's scheduled activity, user's physical, physiological, biological, chemical and emotional quantifiably parameters, and hierarchy thereof; distance travelled measured by an accelerometer, velocity, heart rate, blood pressure, body temperature, sleeping time, duration of phone calls, numbers of outgoing and incoming calls and text messages, identification of calls and callers, number of calls, length of calls, number of unique calls, number and duration of visits in restaurants, and fast food sites, sport's sites including swimming pools, gym, camera photos, location, acquisitions, electrical activity of the brain, mood parameters, including variability and frequency of mood change, increased blood pressure, prolonged skin problems, extreme change in appetite, excess gas, frequent dizziness, gastric ulcer, myocardial infarction, inability to work, nightmares, feeling incompetent in all areas, desire to escape everything, apathy, depression or prolonged anger, excessive tiredness, thinking/talking over and over about the same topic, irritability for no apparent reason, daily distress/anxiety, emotional hypersensitivity, loss of sense of humor, cold hands and/or feet, dry mouth, stomach pain, increased sweating, muscle tension, tightening of the jaw/teeth grinding, transient diarrhea, insomnia, tachycardia (increased heart rate) hyperventilation (increased respiratory rate), sudden or transient increased blood pressure, change in appetite, surge of motivation, sudden enthusiasm, sudden urge to start new projects, memory problems, general malaise without specific cause, tingling of the extremities, feeling of constant physical strain, change in appetite, skin problems, increased blood pressure, constant tiredness, gastritis/gastric ulcer, dizziness/feeling as if floating, excessive emotional sensitivity, self-doubt, constant thought about the same topic, constant irritability, decreased libido, frequent diarrhea, sexual difficulties, insomnia, nausea, tics and any combination thereof.

It is one object of the invention to disclose a method of bio-feedbacking as defined in any of the above claims, wherein said wherein said captive portal is configured to collect and store said subject's data input.

It is another object of the invention to disclose a method of bio-feedbacking as defined in any of the above claims, wherein said wherein said system is either stationary or mobile.

It is another object of the invention to disclose a method of bio-feedbacking as defined in any of the above claims, wherein said wherein said CP comprises an algorithm configured to weigh the results of said data input, with said data of said database.

It is another object of the invention to disclose a method of bio-feedbacking as defined in any of the above claims, wherein said wherein said instructions for electrostimulation comprises at least one of the group consisting of a wearable neurofeedback (NF) system and a wearable neurofeedback system using virtual reality (VR)

It is another object of the invention to disclose a method of bio-feedbacking as defined in any of the above claims, wherein said system comprises at least one EEG electrode configured to stimulate at least one brain area.

It is another object of the invention to disclose a method of bio-feedbacking as defined in any of the above claims, wherein said system mammalian subject is a human patient.

It is another object of the invention to disclose a method of bio-feedbacking as defined in any of the above claims, wherein said system is useful for treating eating disorders.

It is another object of the invention to disclose a method of bio-feedbacking as defined in any of the above claims, wherein said eating disorders are selected from a group consisting non-diagnosed eating disorders, unbalanced eating, uncontrolled eating, industrial eating, obesity, anorexia nervosa, bulimia nervosa, muscle dysmorphia, Binge Eating Disorder, Other Specified Feeding or Eating Disorder, atypical anorexia nervosa, atypical bulimia nervosa, Eating Disorders, disorders with symptoms similar to anorexia or bulimia that do not meet all diagnostic criteria for DSM disorders and any combination thereof.

It is another object of the invention to disclose a method of bio-feedbacking as defined in any of the above claims, wherein said human patient is selected from a group of patients not diagnosed with obesity, patient diagnosed with obesity, patient diagnosed with AD(H)D, patient not diagnosed with AD(H)D, patient diagnosed with eating disorders, and patient not diagnosed with eating disorders.

It is another object of the invention to disclose a method of bio-feedbacking as defined in any of the above claims, wherein said CPM further provides instructions for cannabinoid-based therapy adjunct to said cranial electrode mediated electro stimulation.

It is another object of the invention to disclose a method of bio-feedbacking as defined in any of the above claims, wherein said eating disorders are selected from a group consisting of: Anorexia Nervosa, Bulimia Nervosa, Binge Eating Disorder (BED), Avoidant/Restrictive Food Intake Disorder (ARFID), obesity, unbalanced eating, selective eating, western industrial eating, orthorexia, excessive exercise and any combination thereof.

It is another object of the invention to disclose a method of bio-feedbacking as defined in any of the above claims, wherein said Passive Continuous Input Data comprises at least one of said subject's parameters selected from distance travelled, velocity, heart rate, blood pressure, body temperature, sleeping time, duration of phone calls, number of outgoing and incoming calls and text messages, identification of phone calls and callers, length of calls, WhatsApp messages, Social networks' usage, visits in restaurants, visits in in fast food sites, visits in swimming pools, visits in gym, camera photos, location, acquisitions and any combination thereof.

It is another object of the invention to disclose a method of bio-feedbacking as defined in any of the above claims, wherein said Passive Continuous Input Data is assembled by a device is selected from a group of a mobile phone, a smartphone, a watch, a smart watch, a bracelet, a smart bracelet, a wristband, a smart wristband, a smart band and any combination thereof.

It is another object of the invention to disclose a method of bio-feedbacking as defined in any of the above claims, wherein said Basic Input Data comprises personal details, said personal details are weight, BMI, body fat, muscle mass, height, age and gender.

It is another object of the invention to disclose a method of bio-feedbacking as defined in any of the above claims, wherein said Active Input Data comprises at least one of a personal characterization questionnaire, an eating and diet preferences questionnaire, a "Health promoting questionnaire" and any combination thereof.

It is another object of the invention to disclose a method of bio-feedbacking as defined in any of the above claims, wherein said CP is configured to repeat to collect said data following said treatment of said eating disorders at plurality of time points, to determine whether the subject is responsive; and to recommend the stimulation to be continued if the subject is responsive or to be discontinued is the subject is non responsive.

It is another object of the invention to disclose a method of bio-feedbacking as defined in any of the above claims, wherein said CP further configured to collect said data following said treatment of said eating disorders, at n time points, wherein n is an integer equal of higher than 2, comprising of first time point before start of said treatment of said eating disorders and a second time point at a later time over life of said mammalian subject; further wherein said CMP configured to provide instructions for cranial electrode mediated electro stimulation to said areas in the brain according to a predetermined patient data dependent protocol, and said database provides data related to eating disorders, and said stimulation be continued, if values of said mammalian subject's weight in said input data at second time point are lower than value at said first time point i.e. subject.

It is one object of the invention to disclose a personalized portable system configured for a rapid diagnosis of a mammalian subject, said system characterized by:
a. an EEG wearable device configured for both sensing and for stimulating defined area of patient's brain;
b. a user-derived, internal-data source, captive portal data input (CP); said data comprises basic input data, algorithm-based questionnaires; and measurements of said EEG;
c. a graphical user interface (GUI); and
d. a computer processing manager (CPM) for processing both said internal data and external data, interconnected with said CP, said database and said GUI; said CPM is configured to instruct cranial electrode mediated electro-stimulation to stimulate said area of patient's brain according to said patient-data driven stimulating-protocol.

It is one object of the invention to disclose a method for rapid diagnoses of a mammalian subject, said method comprising:
a. providing a user derived module, comprising an internal-data source captive portal data input (CP); said data comprises basic input data, algorithm-based questionnaires; and measurements of said EEG;
b. providing an EEG wearable device configured for both sensing and for stimulating defined area of patient's brain;
c. providing a external-data source database;
d. providing a graphical user interface (GUI); and
e. providing a computer processing manager (CPM) for processing both said internal data and external data, interconnected with said CP, said database and said GUI; said CPM is configured to instruct cranial electrode mediated electro-stimulation to stimulate said area of patient's brain according to said patient-data driven stimulating-protocol.

BRIEF DESCRIPTION OF THE FIGURES

The accompanying drawings, which are included to provide a further understanding of the invention and are incorporated in and constitute a part of this specification, illustrate embodiments of the invention and together with the description serve to explain the principles of the invention FIG. 1 A system for diagnosing and determining a treatment protocol for mammalian subject, according to an embodiment of the invention.

DETAILED DESCRIPTION OF PREFERRED EMBODIMENTS

Figure 1:
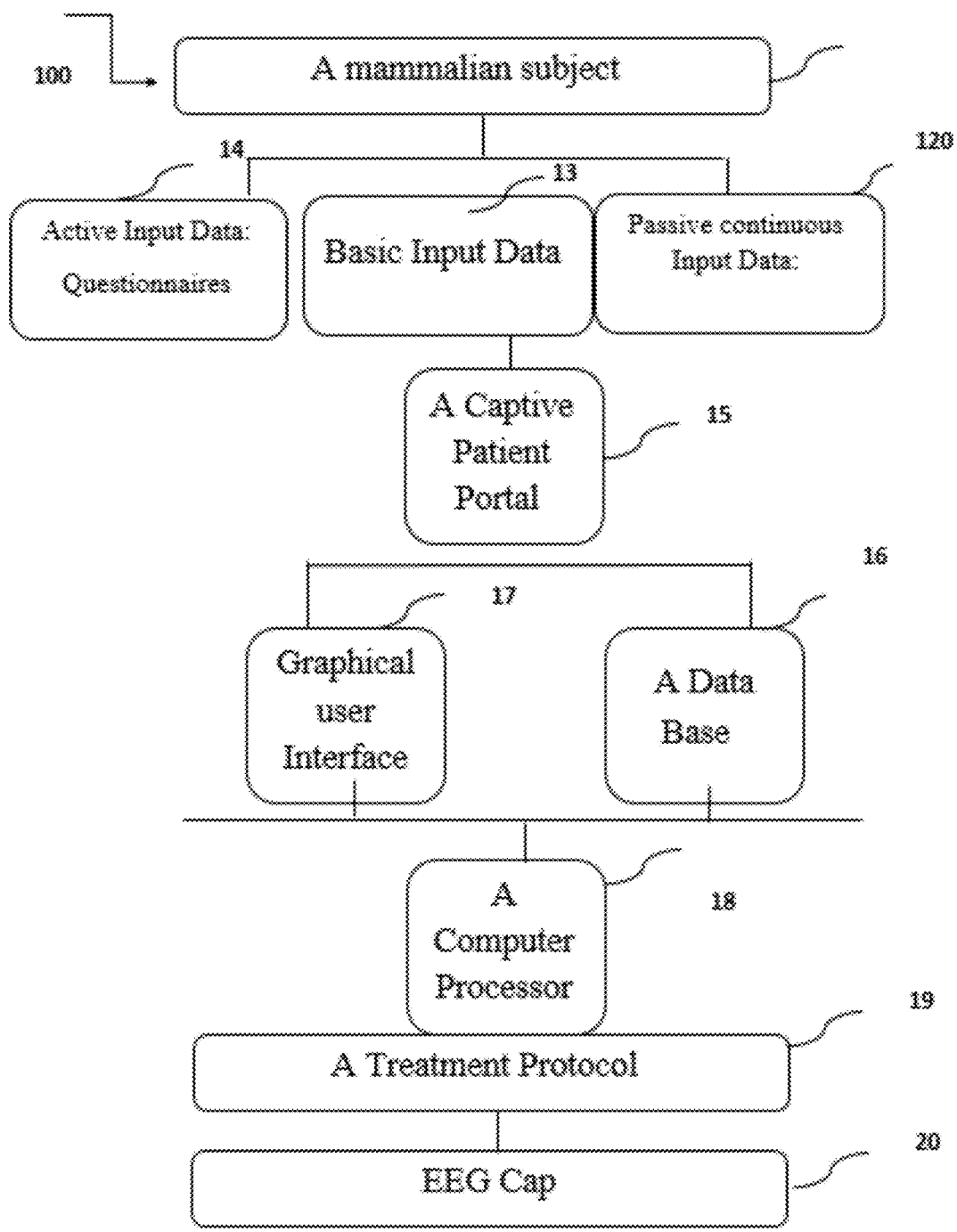

The following description is provided, alongside all chapters of the present invention, so as to enable any person skilled in the art to make use of the invention and sets forth the best modes contemplated by the inventor of carrying out this invention. Various modifications, however, are adapted to remain apparent to those skilled in the art, since the generic principles of the present invention have been defined specifically to provide a portable personalized neurofeedback computerized system for diagnosing and treating eating disorders, unbalanced eating, and uncontrolled behavior in mammalian subjects.

The principles the current invention are as follows:
a. The system is an End-to-End eHealth smart platform based on AI & Big Data for analysis, diagnosis and therapy of types of behavioral disorders, addictions.
b. The system is designed, inter alia, for users (subjects), mammals, animals, children or adults, who are overweight, and for users suffering inter alia of eating disorders, unbalanced eating, uncontrolled eating or obesity, ADHD, addictions, ADD, eating behaviors, depression, anxiety, autism, as well as eating accompanying diseases anxiety addictions, pain, sexuality and fertility, fibromyalgia performance, sleep disorders.
c. The system is designed to analyze and diagnose the disorder or behavior, as well as to select an appropriate treatment modality and offering a treatment protocol based on bio-feedbacking of selected brain areas, by an EEG electrode located in the brain area according to the results of the diagnosis.
d. The analysis and diagnosis of the system is a rapid process, performed by capturing patient data which includes mainly several specifically designed questionnaires, which may be combined with EEG measurement, to increase validity of diagnosis.
e. The system comprises a unique algorithm that summarizes and weighs each mammal's personal data, and the results of a combination of unique specific questionnaires which were validated in clinical setting.
f. According to the results of the algorithm, the system offers personal treatment for each patient,
g. The treatment is based on biofeedback, either EEG-based neurofeedback, HEG-based neurofeedback or QEEG neurofeedback. Thus the QEEG is used as a diagnostic product and as a treatment.
h. The results of the treatment are examined individually after several neurofeedback treatments (usually after 15 treatments, but not limited); and according to the individual examination, it is recommended to continue with the original protocol or to apply a new treatment protocol,
i. The system is designed for clinics or home care and offers an enjoyable treatment that increases motivation, and adherence to treatment
j. The system is designed as a single treatment or as a supplement (or an adjunct treatment) to existing treatments such as bariatric surgery, psychopharmacologic treatment, any diet regimens, weight control, and treatments for obstructive sleep apnea as a supplement or adjunct treatment to psychological, personal training such as coaching, nutrition, CBT, guided imagination, tranquilizers, and drugs.

Advantages of the current invention: To date, subjective questionnaires or sophisticated objective physiological scans have been used to assess emotional or behavioral cognitive disorders. The current invention is an accessible solution for every clinic (and even home) of a disorder diagnosis algorithm that combines a simple and inexpensive QEEG and questionnaire. Its advantage lies in simplifying the process together with uncompromising precision. The current invention have been tested mainly for obesity, one of the most disturbing disorders in the Western world today. The study included analyzing the knowledge about patterns of brain activity relevant to the area of the disorder, mapping norms in the population in this area, constructing a specific algorithm for evaluating the subject with respect to the norms, and proving the effectiveness of brain training based on the assessment process. The efficacy of QEEG for diagnosis and treatment has so far been proven to be most effective for ADHD, but this disorder has not yet developed an algorithm for diagnosing the disorder that incorporates a QEEG questionnaire, and therapists offer only a partial solution for diagnosis and treatment. Following the strong link between ADHD and obesity, the current patent study focused on obesity disorder and demonstrated both the validity and cost-effectiveness of using the algorithm and the effectiveness of QEEG-based therapies derived from the algorithm-based assessment tool. As a result, the current invention includes a prepared algorithm for the diagnosis and treatment of brain-based training for obesity disorder, and a template for constructing additional kits for other disorders. Its technological innovation is expressed in the use of VR to increase the user experience, the use of BIG DATA for the continuous collection of data from the population for the purpose of monitoring norms, the AI for monitoring and adapting the user care program, and the management of a hybrid file which synchronizes with clinic patients and all other users.

The current invention serves as a basis and platform for diagnosing and treating the following symptoms: eating disorders, un-controlled eating accommodating diseases Anxiety Addictions pain Sexuality and fertility problems, fibromyalgia performance, sleep disorders, AD (H) D, ADD, O.C.D, addictions, and autism.

The main advantages of the current invention are:
a. The current invention is a simple (yet sophisticated in its structure) and efficient computerized system for evaluating and diagnosing mammalian subjects, based on a short and convenient questionnaire, followed by an algorithm and backed by EEG; EEG As needed
b. The current invention offers a rapid diagnosis with a rapid recommendation for a treatment protocol, with less need for an intensive and elaborating training period for the medical care givers, as well as medical care analysts and evaluators. The target care givers are, for example, physicians, psychologists, who will use the system to receive algorithmic technological support for the characterization and behavior characterization, according to which a therapeutic and/or drug and/or nutritional recommendation and/or cannabis and/or neurofeedback will be recommended. Furthermore, it should be noted that drug recommendations should be tailored to information about a person's brain activity, such as simulators administration to a subject with excess beta brain activity will cause serious side effects.
c. Combining EEG (or QEEG or HEEG) with questionnaire-based algorithm, the current invention uses the same EEG based system as a rapid diagnosis tool, as well as a tool for biofeedback (or neurofeedback).
d. The current invention can serve as platform for a variety of behavioral-based disease or disorders, by designing and validating a specific "package" system comprising a personal questionnaire as well as the relevant algorithm; which will provide a neurofeedback treatment protocol;
e. The current invention is less expensive supplement to the insurance group, the health funds By reducing the patient's intake time and by correcting the diagnosis in combination with risk management for the patient and the therapist f. An hybrid medical model: Tracking the rate of patient recovery, and efficient remote communication with the patient in order to respond to their questions. Possibility to integrate patient personal medical file g. The current invention is a portable invention that can be used at the clinics and can be used at home, as the system is connected to all kinds of digital devices, inter alia smartphones, tablets, laptops, PCs, via a specific program or a web application.

h. In summary, the current invention can identify an abnormal behavior, a dominant region, and regional relations, and the relevant measures are relevant to the therapist, and in each field on which the questionnaire will be constructed and statistics will be prepared on it, AI & Big Data for Analysis, Diagnosis and Therapy of Types of Addiction.

i. Remote diagnosis of diseases allows you to perform a diagnosis at home—without reaching the clinic, as well as the treatment using neurofeedback by an EEG electrode located in the brain area according to the results of the diagnosis.

The term eating disorder refers hereinafter to a mental disorder defined by abnormal eating habits that negatively affect a person's physical or mental health. Eating disorders is selected from a group selected from disorders such as, anorexia nervosa, bulimia nervosa, binge eating disorder, and their variants or people suffering from abnormal eating which disturbs their life quality.

The system is also suitable for subjects who suffer of unbalanced eating and nutritionally-unsatisfied eating a variety of unspecified eating disorders, as described below, and uncontrolled behavior.

The term BMI refers herein after to Body mass index, which is a value derived from the mass (weight) and height of a person. The BMI is defined as the body mass divided by the square of the body height, and is universally expressed in units of kg/m2, resulting from mass in kilograms and height in meters. The BMI is a convenient general value used to broadly categorize a person as underweight, normal weight, overweight, or obese based on tissue mass (muscle, fat, and bone) and height. (see Table 1).

TABLE 1

BMI Categories

| Category | BMI (kg/m$^2$) from | to | BMI Prime from | to |
|---|---|---|---|---|
| Severely underweight | 15 | 16 | 0.60 | 0.64 |
| Underweight | 16 | 18.5 | 0.64 | 0.74 |
| Normal (healthy weight) | 18.5 | 25 | 0.74 | 1.0 |
| Overweight | 25 | 30 | 1.0 | 1.2 |
| Obese Class I (Moderately obese) | 30 | 35 | 1.2 | 1.4 |
| Obese Class II (Severely obese) | 35 | 40 | 1.4 | 1.6 |
| Obese Class III (Very severely obese) | 40 | 45 | 1.6 | 1.8 |
| Obese Class IV (Morbidly Obese) | 45 | 50 | 1.8 | 2 |
| Obese Class V (Super Obese) | 50 | 60 | 2 | 2.4 |
| Obese Class VI (Hyper Obese) | 60 | | 2.4 | |

The term obesity refers hereinafter to a chronic condition clinically defined in terms of body mass index (BMI), a person is considered obese if their BMI is above 30 kg/m$^2$ Obesity is a major health problem worldwide and has reached epidemic proportions in both developed and developing countries making it an extremely important public health issue. Obesity is associated with risk factors for many medical complications and comorbidities such as cardiovascular diseases, osteoarthritis, hypertension, dyslipidemia, hypercholesterolemia, type-2 diabetes, obstructive sleep apnea syndrome, diabetes mellitus, non-alcoholic fatty liver disease, reduced lung function and increased risk of cancers. The condition can also present negative psychological impact resulting in social stigma, mental health and self-esteem issues, and poorer quality of life.

The term Basic Input Data is defined hereinafter as personal details, the personal details are weight, height, BMI, body fat, muscle mass, age and gender, The term Active Input Data is defined hereinafter as several types of questionnaires: a personal characterization questionnaire, AD(H)D classification questionnaire and a health promoting questionnaire The term personal characterization questionnaire defined hereinafter as a questionnaire characterizing a type of subject.

The term AD(H)D classification questionnaire, defined hereinafter as a questionnaire characterizing type of user, by the user' administrative functions including impulsivity, procrastination, ambition, eating and activity and sleep habits questionnaire. Worries, Hypersensitivity Pain Anxiety Emotional Addiction And later on, the questions will be changed to other areas based on the same method presented for the current invention, further diagnosing attention disorders, identifying problems with sexuality and fertility, etc. Eating disorders un-controlled eating accompaniment diseases, anxiety addictions, pain, sexuality and fertility problems, fibromyalgia performance, sleep Disorders AD (H) D, ADD, OCD Addictions autism The term health promoting questionnaire defined hereinafter as a questionnaire designed to diagnose health habits; or eating and diet preferences, nutrition habits, eating habits and eating patterns of the subject user; as well as information regarding the nutritional deficiencies and sensitivity to food products or food elements. The health promoting questionnaire provides the statements which include results of AD(H)D classification questionnaire of the same user.

The term Passive Continuous Input Data, defined hereinafter as least one of the subject's parameters selected from distance travelled, velocity, heart rate, blood pressure, body temperature, sleeping time, duration of phone calls, number of outgoing and incoming calls and text messages, identification of phone calls and callers, length of calls, WhatsApp messages, Social networks' usage, visits in restaurants, visits in in fast food sites, visits in swimming pools, visits in gym, captured photos, locations, an eating log behavior, acquisitions, and any combination thereof.

The term uncontrolled behavior is defined hereinafter as behavior which cannot be stopped or made it less extreme, mainly by the behavior him/herself. Uncontrolled behaviors comprise, inter alia, addictions to eating, smoking, shopping, work, etc.

The term ADHD refers hereinafter to Attention deficit hyperactivity disorder, a mental disorder of the neurodevelopmental type.

The term Behavioral Scoring Scale (BSS) refers hereinafter as the scored behavior and daily living actions of the user.

The Health promoting questionnaire refers hereinafter to a questionnaire that measures the level of health of the subject According to the World Health Organization, health is a holistic view of a variety of behaviors, all of which are expressed in the questionnaire.

The health promoting questionnaire is based on a lifestyle questionnaire and symptoms from which the client suffers, including inter alia quality of sleep, pain, or obesity.

The term biofeedback refers hereinafter to the process of gaining greater awareness of many physiological functions primarily using instruments that provide information on the activity of those same systems, with a goal of being able to manipulate them at will. Some of the processes that can be controlled include brainwaves, muscle tone, skin conductance, heart rate and pain perception. In biofeedback, the subject is connected to electrical sensors that assist the subject to receive information (feedback) about the subject's body (bio).

The terms electroencephalograph or EEG refer hereinafter to a device which measures the electrical activation of the brain from scalp sites located over the human cortex. The EEG shows the amplitude of electrical activity at each cortical site, the amplitude and relative power of various wave forms at each site, and the degree to which each cortical site fires in conjunction with other cortical sites.

The terms QEEG or Q-EEG refer hereinafter to Quantitative EEG. Q-EEG is an extension of classical EEG analysis. In a Q-EEG, the data from the raw EEG are summarized, evaluated and displayed as a graphic.

The terms hemoencephalography or HEG biofeedback refer hereinafter to a functional infrared imaging technique. As its name describes, it measures the differences in the color of light reflected back through the scalp based on the relative amount of oxygenated and unoxygenated blood in the brain. Research continues to determine its reliability, validity, and clinical applicability. HEG is used to treat ADHD and migraine, and for research The terms neurofeedback or NF refer hereinafter to a type of biofeedback that measures brain activity in real time using electro-electrophysiology (EEG) or hemoencephalography (HEG) or QEEG to teach and train a patient to control his brain waves by providing feedback (Positive "feedback") for a desired type of brain activity and negative feedback on an undesirable activity type.

According to the above, the term neurofeedback refers hereinafter either to EEG-based neurofeedback, HEG-based neurofeedback, or QEEG-based neurofeedback.

The term "ADHD" refers hereinafter to Attention deficit hyperactivity disorder, a mental disorder of the neurodevelopmental type. Attention-deficit/hyperactivity disorder (ADHD) is a common neurodevelopmental disorder. The main symptoms are inattention, hyperactivity, and impulsivity.

ADHD is also characterized by problems paying attention, excessive activity, or difficulty controlling behavior which is not appropriate for a person's age. The symptoms appear before a person is 12 years old, are present for more than six months, and cause problems in at least two settings (such as school, home, or recreational activities). [In children, problems paying attention may result in poor school performance. The behavioral and cognitive symptoms of ADHD can have a negative and significant effect in regulating food. Maintaining a high level of awareness of inner states, especially when distracted by other activities, can be a particularly difficult challenge for a person with ADHD. Many people with ADHD and eating disorders report that they often skip meals because they have not noticed hunger, or know how to stop eating only when they feel "too full." Dietary regulation also requires a high level of organization and planning, another area of difficulty for people with ADHD. Proper nutrition at appropriate times requires a series of activities, including preparing a shopping list, buying food, and preparing it. It is also necessary to be sensitive to the passage of time, to know that it is time to refuel Clinical experience shows that as the rules are ambiguous or ambiguous, it is difficult for people with ADHD to make good decisions. On a daily basis, people are bombarded with a wide range of contradictory and confusing suggestions of how to eat right. Furthermore, food provides immediate reward when the results of diet are both delayed and abstract. People with ADHD tend to be dominated by the moment, acting, and only afterwards are filled with remorse for their inability to foresee. People with ADHD generally consume high levels of stimulation to feel focused and emotionally balanced. For many, being without irritation creates an uncomfortable feeling of irritability, boredom or fatigue that temporarily relaxes by eating. Because food is so available, it is difficult for many people to resist the need to eat if they find themselves without stimulated.

Eating disorders related to ADHD patients Dysfunction in ADHD management and the relation to overweight: The basic characteristics of ADHD, which include inattention, hyperactivity, and impulsivity, are associated with dysfunction. High levels of obesity were observed in children, adolescents and adults with ADHD. People with ADHD tend to interpret their restlessness, boredom, or fatigue as a state of hunger, and therefore eat more than they need. The result is uncontrolled obesity. In addition, the main characteristic of ADHD is the inability to stop and stop thoughts, to stop even destructive behaviors. The internal control system that stops harmful behaviors in every person does not work in people with ADHD, and in the case of eating, the result is overeating.

Lack of sleep Patients with ADHD also have many other symptoms, including sleep problems, which are reported to occur in 25-55% of patients with ADHD). In a recent systematic literature review, sleep problems were reported to be among the most common co-morbidities associated with ADHD, see Instanes et al. (2016). Adult ADHD and comorbid somatic disease: a systematic literature review. *J. Atten. Disord.* [Epub ahead of print]. 10.1177/1087054716669589, incorporated herein as a reference. Poor sleep often leads to inattention/lack of concentration and mood swings, symptoms also typically seen in ADHD. Thus, it has been suggested that some patients may have been misdiagnosed with ADHD instead of a primary sleep disorder. Alternatively, sleep problems may be considered an intrinsic feature of ADHD. Moreover, some patients may have co-morbid ADHD and sleep disorder. Overall, the distinction between having ADHD with sleep problems, having a sleep disorder with ADHD-like symptoms, or having co-morbid ADHD and sleep disorder is blurred and needs more systematic exploration, see Bjorvatn, B., et al (2017). Adults with Attention Deficit Hyperactivity Disorder Report High Symptom Levels of Troubled Sleep, Restless Legs, and Cataplexy. *Frontiers in Psychology,* 8, 1621, incorporated herein as a reference.

Most studies investigating sleep problems among ADHD patients have been performed in children/adolescents (Philipsen et al., 2006; Yoon et al., 2012; Bioulac et al., 2015; Hvolby, 2015). However, it has been proposed that sleep-related problems are even more common in adults than in children with ADHD, and that the type of sleep problems may depend on age (Surman et al., 2009; Yoon et al., 2012; Hvolby, 2015).

Emotional Eating: Eating is comforted Eating serves as a "flight" and as a refuge from daily difficulties. Attention deficit disorder creates a reality of coping with many difficulties during the day. Difficulties are evident in all areas of life: study, work, interpersonal, social, marital, etc. To cope with the experience of failure that accompanies them, ADHD may find comfort in food, thus being exposed to "emotional eating," which increases the risk of obesity. "Emotional eating" is also characteristic of people with low self-esteem, which is also associated with attention deficit disorders. Among people with ADHD who are not treated with drugs such as Ritalin, the level of dopamine is not balanced, and they are at greater risk of obesity than those treated with Ritalin. However, among those treated with medication, obesity may develop as a result of an eating disorder.

Impulsivity: Hurry to eat and forget to plan Impulsive behavior and difficulty in self-restraint are risk factors for uncontrolled eating, leading to obesity. Impulsivity is also joined by procrastination, which causes people with attention deficit disorder to prepare a nutritious and planned meal. For example, when they want to make a salad, the brain creates stagnation because of the tasks involved in preparing it, and instead they eat ready and available food which might not be as healthy.

Emotional dysfunction in children and overweight A study of 57 children between the ages of 2 and 5.5 years of age found that those with a low emotional regulation and less inhibitory control, and more sensitive to reward, were more likely to become obese at the age of 5.5. In other words, difficulties in self-regulation at a young age are a risk factor for obesity in childhood.

The current invention proposes a sensible and appropriate eating plan that replaces bad eating habits that raise symptoms of ADHD as disorder, impulsivity, and disorder of self-awareness ADHD and Eating Disorders Attention Deficit Hyperactivity Disorder (ADHD) is one of the most common neurodevelopmental disorders of childhood and has a worldwide prevalence of 5% in school-age children. The symptoms of ADHD persist in adults in up to 65% of cases and the prevalence of ADHD in adults is estimated at 2.5%. Despite the high prevalence of the disorder, fewer than 20% of adults with ADHD are diagnosed or treated. Moreover, up to 90% of adults with ADHD have comorbid psychiatric disorders, which may obscure the symptoms of ADHD. Depression and other mood disorders, anxiety, personality disorders and substance use disorders (SUDs), in addition to oppositional defiant disorder, sleep problems and learning disabilities are often comorbid with ADHD. It has also been reported that there is an association between ADHD and eating disorders (EDs). There is a consistent moderate strength of evidence that ADHD is positively associated with disordered eating and with specific types of disordered-eating behaviour, in particular, overeating behaviour. In addition, there is evidence that impulsivity is positively associated with BN symptoms. see Kaisari, P., Dourish, C. T, & Higgs, S. (2017). *Attention Deficit Hyperactivity Disorder (ADHD) and disordered eating behavior: A systematic review and a framework for future research. Clinical psychology review*, 53, 109-121.

There is a partial overlap between ADHD and significant overweight. According to various studies, the proportion of significantly overweight adults in ADHD is estimated at 29.4% (33% of adults in the general US population). The proportion of adults with ADHD among those with significant overweight is estimated to be between 26% and 61% (4% of adults in the general US population).

A number of explanations point to a link between the aspects of inattention and impulsivity (and less hyperactivity) and significant overweight:

a. It may be a similar biological mechanism of low dopamine, which causes overeating;

b. Impulsivity and the inability to delay the urge to eat cause overeating;

c. The lack of inhibitions reinforces the tendency to overeating; and d. Deficiency in managerial functions prevents the planning ability of eating and behavioral patterns of health and makes it difficult to adhere to regular eating patterns Neurofeedback is one of the suggested means for treating various neurological syndromes, including ADHD.

The effectiveness of QEEG for diagnosis and treatment has so far been proven to be the best for ADHD, but an algorithm has not yet been developed to diagnose this disorder, which incorporates a QEEG questionnaire, and therapists offer only a partial solution to diagnosis and treatment. Following the strong link between ADHD and obesity, the current patent study focused on obesity disorder and demonstrated both the validity and cost-effectiveness of using the algorithm and the effectiveness of QEEG-based therapies derived from the algorithm-based assessment tool. As a result, the patent includes a prepared algorithm for the diagnosis and treatment of brain-based training for obesity disorder, and a template for constructing additional kits for other disorders.

Furthermore, the system manages behavior as well as a disease state, through brain training for focusing and concentrating, as well as through load reduction technology and therapeutic focus The system decreases cognitive load by creating habits and a daily agenda for each of the users.

In cognitive psychology, cognitive load refers to the effort being used in the working memory.

Heavy cognitive load can have negative effects on task completion; a heavy cognitive load typically creates error or some kind of interference in the task at hand. It is also important to note that the experience of cognitive load is not the same in everyone. The elderly, students, and children experience different, and more often higher, amounts of cognitive load.

High cognitive load in the elderly has been shown to affect their center of balance. With increased distractions and cell phone use students are more prone to experiencing high cognitive load which can reduce academic success. Children have less general knowledge than adults which increases their cognitive load. Recent theoretical advances include the incorporation of embodied cognition in order to predict the cognitive load resulting from embodied interactions.

Prolonged cognitive load can cause also metal fatigue, see Mizuno, K, et al (2011). *Mental fatigue caused by prolonged cognitive load associated with sympathetic hyperactivity. Behavioral and brain functions*, 7(1), 17, incorporated herein as a reference.

Cognitive load as well flood of stimuli affects the sense of stress.

Thus, routine and tasks clean-up noise, by focusing.

Additionally, the system improves recovery performance by prevention of abandonment for optimal disease management, by handling user's control. Control is persistence and preventing abandonment. Thus, training in NF is expected to improve control over management functions which further prevents abandonment and inconsistency.

NF training is expected to improve perseverance in weight loss (such as prolonging the process of average weight loss in bariatric patients), as well as to increase perseverance in drug users in general and in weight loss in particular (e.g. slimming drugs, diabetes, nutritional supplements etc.).

Furthermore, the system enables improving Emotional intelligence. Emotional intelligence (EI), also known as emotional quotient (EQ) and Emotional Intelligence Quotient (EIQ), is the capability of individuals to recognize their own emotions and those of others, discern between different feelings and label them appropriately, use emotional information to guide thinking and behavior, and manage and/or adjust emotions to adapt to environments or achieve one's goal. Studies have shown that people with high EI have greater mental health, job performance, and leadership skills although no causal relationships have been shown and such findings are likely to be attributable to general intelligence and specific personality traits rather than emotional intelligence as a construct.

When a person is in a cognitive load state, his emotional intelligence function is low.

The importance of persistence in taking medications is also preventing the aggravation of a chronic disease such as diabetes, blood pressure, and of course, improving the lifestyle.

Therefore, training by a prefrontal NF for the purpose of improving control is intended to increase the percentage of perseverance in the prescribed treatment and/or its results, i.e., the persistence of health in accordance with the definition World Health Organization (WHO).

Nonadherence This is a common phenomenon. Therefore, it is often investigated and referred to as "non-adherence" or "non-compliance" to the dosage and timing of the drug therapy given here.

Behaviors such as forgetfulness, procrastination, and persistence difficulties sometimes look like attention disorders and lead to abandonment from therapy. In this situation we must identify the dominant factor that creates "psychological forgetting" and/or states of procrastination and abandonment due to the difficulty in coping with the overflow of stimuli from other areas of the brain, not necessarily because of attention deficit disorder in its classical definition.

Managerial functions Managerial functions are a collection of high cognitive skills that enable control and control of behavior, thought and emotion and thus help achieve different goals. Management functions are primarily required in unconventional functions, and in new and complex tasks. Management functions include a broad umbrella of cognitive skills, including: delayed response, working memory, emotional control, initiative, flexibility of thought, transitions, persistence, organization, planning, problem solving and control.

Main managerial functions are:
a. Inhibition—The ability to stop behavior, action or thought in a timely manner. Difficulty in this skill leads to impulsivity. It is difficult to stop and think before action, difficulty waiting in line, difficulty in voting, etc.
b. Transitions—the ability to switch modes freely and respond in a compatible and flexible manner. Difficulty in this skill may be expressed in difficulties in new situations such as changes in the daily routine, difficulties in transition to a new educational framework, and response to unexpected events.
c. Emotional control—the ability to regulate emotions. Difficulty in this skill may be expressed in outbursts of anger, unregulated emotional response (high or low intensity), etc.
d. Initiative—the ability to start a task or action. Difficulty with this skill may be expressed in difficulty starting homework, postponing tasks, etc.
e. Work Memory—The ability to hold information in memory for as long as it takes to complete the task. Difficulty in this skill may be expressed in the difficulty of performing all the instructions given by the teacher, forgetting objects, difficulty remembering complex rules of the game, etc.
f. Planning/organizing—The ability to perform complex task requirements. Difficulty in this skill may make it difficult to plan a party, difficulty in planning the afternoon routine, difficulty in ordering a friend in advance, etc.
g. Organization—the ability to maintain an organized environment and prearrange all the materials and tools required for carrying out a task. Difficulty in this skill may be expressed in the loss of parts of the game, difficulty in organizing the learning environment/game when finished, the room is not organized and so on.

Testing—Ability to check the quality of your workmanship and correct if necessary. Difficulty in this skill may be expressed in passing an examination without checking the answers, difficulty in organizing a school bag according to a given system, a sloppy performance, etc.

U.S. Pat. No. 9,867,546 to Facense Ltd discloses an expensive and not available wearable devices for taking symmetric thermal measurements. The device includes several thermal cameras coupled to a frame worn on a user's head. A first thermal camera takes thermal measurements of a first region of interest that covers at least a portion of the right side of the user's forehead. A second thermal camera takes thermal measurements of a second ROI that covers at least a portion of the left side of the user's forehead. The first and second thermal cameras are not in physical contact with their corresponding ROIs, and as a result of being coupled to the frame, the thermal cameras remain pointed at their corresponding ROIs when the user's head makes angular movements. Korean patent application No. 20080039805 to Hee discloses an apparatus and a method for neuro feedback are provided to maximize effect of medical treatment on psychogenic diseases such as melancholia or ADHD by offering optimum neuro feedback training based on distribution of brain waves. An apparatus for neuro feedback includes a first measuring unit, a map generating unit, a symptom detecting unit, and a content determining unit. The first measuring unit obtains brain wave signals corresponding to a plurality of parts of a subject brain. The map generating unit generates a brain map indicating amplitude distribution of a brain wave component corresponding to a predetermined frequency domain, on the basis of the brain wave signals. The symptom detecting unit detects symptoms of a subject based on the generated brain map. The content determining unit determines neuro feedback training contents suitable for the detected symptoms.

U.S. Pat. No. 9,895,077 and application No. US2011004412 to Elminda ltd discloses a method of analyzing neurophysiological data is disclosed. The method comprises: identifying activity-related features in the data, constructing a brain network activity (BNA) pattern having a plurality of nodes, each representing a feature of the activity-related features, and assigning a connectivity weight to each pair of nodes in the BNA pattern; Similarly it discloses a method for functional analysis of neurophysiological data by decomposing neurophysiological data and EEG signal to form a plurality of signal features. The signal features may then optionally be analyzed to determined one or more patterns.

US patent application No. 20150157235 to Jelen et al. discloses systems and methods are provided for performing neurometric evaluation of Quantitative Electro Encephalogram (QEEG) data, derived from Dry Sensor technology, as opposed to the use of any types of conventional paste/gel and silver/silver chloride sensors. Their technology relates to a method for assessing brain functioning, to promote and advance early screenings, the method comprising of (i) active electrode (also called dry sensor) technology for performing the signal acquisition, (iii) at specific placement or predetermined placement locations on the scalp, and (ii) incorporating Quantitative EEG statistical methods to derive prognostic data that assists in planning treatments.

WO2003075762 by ADHD Solutions Ltd. discloses a method for diagnosis and for treatment of ADHD and ADD, based on computer-generated visual stimuli. The method discloses teaches diagnosis of ADHD by steps of (a) subjecting a patient to a plurality of computer generated visual stimuli; and the computer generated visual stimuli are comprised of at least nine tasks selected from the following types of task: a sustained attention test, a visual search, a flanker task, a cost-benefit paradigm with endogenous cues, a cost-benefit paradigm with exogenous cues, a stroop task, a stroop-like task, a global-local task or a switched global-local task; (b) measuring the response time and accuracy of response of the patient for each of the tasks; (c) comparing the measurements for each task with measurements generated from healthy individuals; (d) generating an attentional profile for the patient based on the comparison; and (e) diagnosing the presence or absence of ADHD or ADD in the patient.

The main components of the system are a Captive Portal for the subject's (CP) data input, wherein the input comprises Basic Input Data, Passive Continuous Input Data and Active Input data, a database comprising data, a Computer Processing Manager (CPM) for processing the patient data and the database, a Graphical User Interface (GUI) for interfacing with a user, and an EEG cap for stimulating predetermined areas in the brain. The CPM is interconnected to the CPP, The database, the GUI and the CPM provide instructions for cranial electrode mediated electro stimulation to areas in the brain according to a predetermined patient data dependent protocol, and the database provides data related to obesity and eating disorders.

Specifically, the home-based system of the present invention (100) comprises a Captive Portal (CP, 15) for the subject's data input, wherein the input comprises Basic Input Data (13), Passive Continuous Input Data (12) and Active Input Data, while the CP (15) analyzes the subject' inputs The inputs are characterized by Basic Input Data (13), comprises personal details, the personal details are weight, height, BMI, body fat, muscle mass age and gender, Active Input Data (14), comprises several types of questionnaires, e.g., a personal characterization questionnaire aimed to characterize a type of subject, the at least one personal questionnaires is selected form a group consisting AD(H)D classification questionnaire, ADHD with an emphasis on managerial functions including impulsivity, procrastination, ambition questionnaire, eating and activity and sleep habits questionnaire, health promoting questionnaire designed to diagnose health habits; or eating and diet preferences questionnaire, and any combination thereof; an eating and diet preferences questionnaire, in order to characterize the nutrition habits, eating habits and eating patterns of the subject; as well as information regarding the nutritional deficiencies and sensitivity to food products or food elements; Passive Continuous Input Data (12), collected and assembled by a device selected from a group of EEG, QEEG, HEG, a camera, a body fat monitor a mobile phone, a smartphone, a watch, a smart watch, a bracelet, a smart bracelet, a wristband, a smart wristband, or a smart band. Motion sensors available in off-the-shelf smartphones can capture physiological parameters of a person during stationary postures, even while being carried in a bag or a pocket.

A non-limiting example of the camera is an action camera, autofocus camera, camcorder, camera phone, digital camera, disposable camera, folding camera, helmet camera, high-speed camera, infra-red camera, instant camera, keychain camera, live-preview digital camera, movie camera, multi-plane camera, pocket camera, pocket video camera, point-and-shoot camera, polaroid camera, pool safety camera, professional video camera, reflex camera, remote camera still camera, still video camera, subminiature camera, system camera, thermal imaging camera, thermographic camera, toy camera, video camera, webcam and any combination thereof.

A non-limiting example of the camera is a camera comprising voice sensors, which are activated on appearance of predetermined voices related to addictive and uncontrolled situations as: cutlery, plates, jettons on gambling tables, drinking, chewing, smoke inhalations and any combination thereof.

Figure 2:
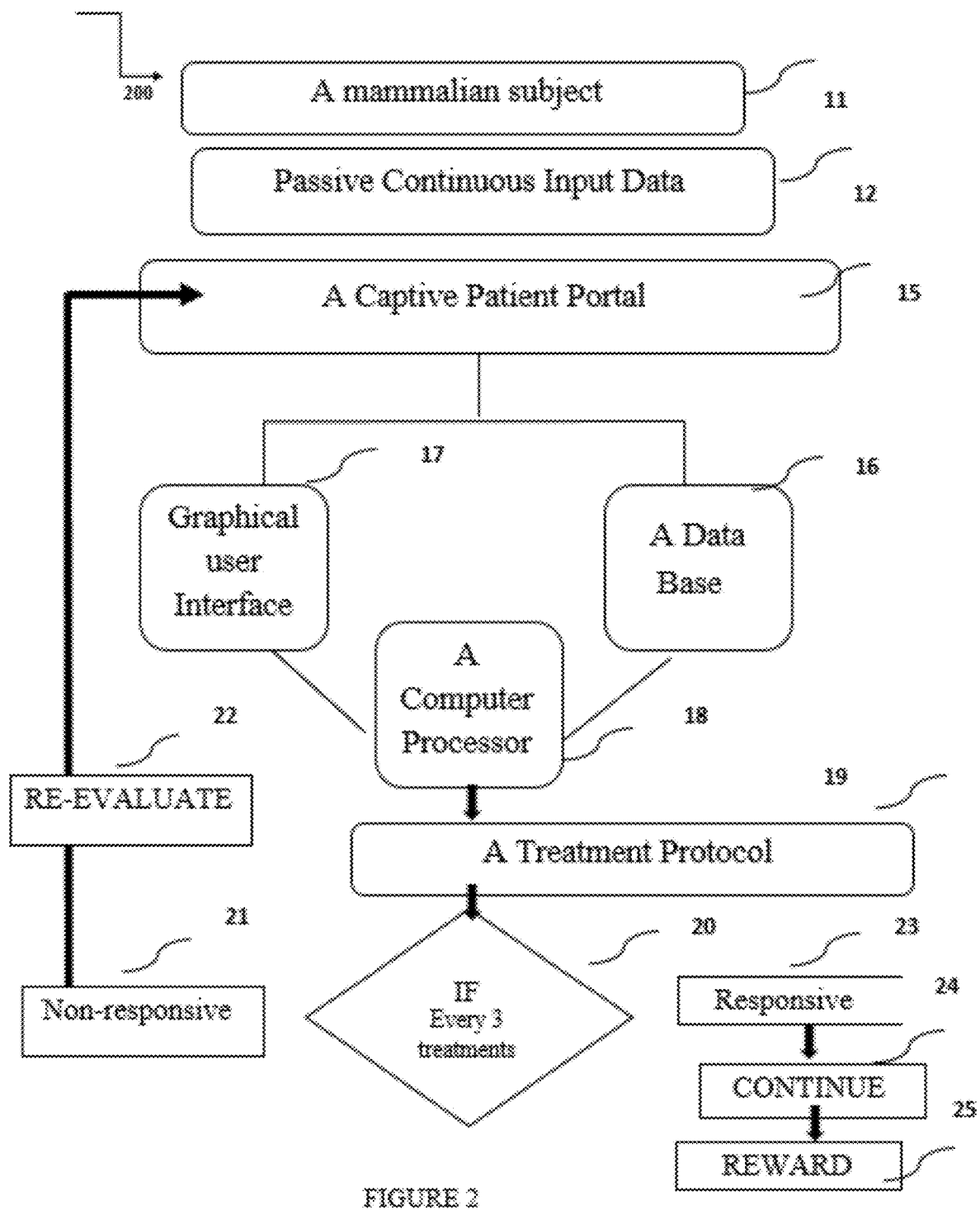
FIG. 2. A method for monitoring mammalian subject, by Passive Continuous Input Data, and assessing the need to re-evaluate or continue the current treatment protocol, according to the accumulated Continuous Input Data once every 3 treatments, according to another embodiment of the invention.
Figures 2, 3:
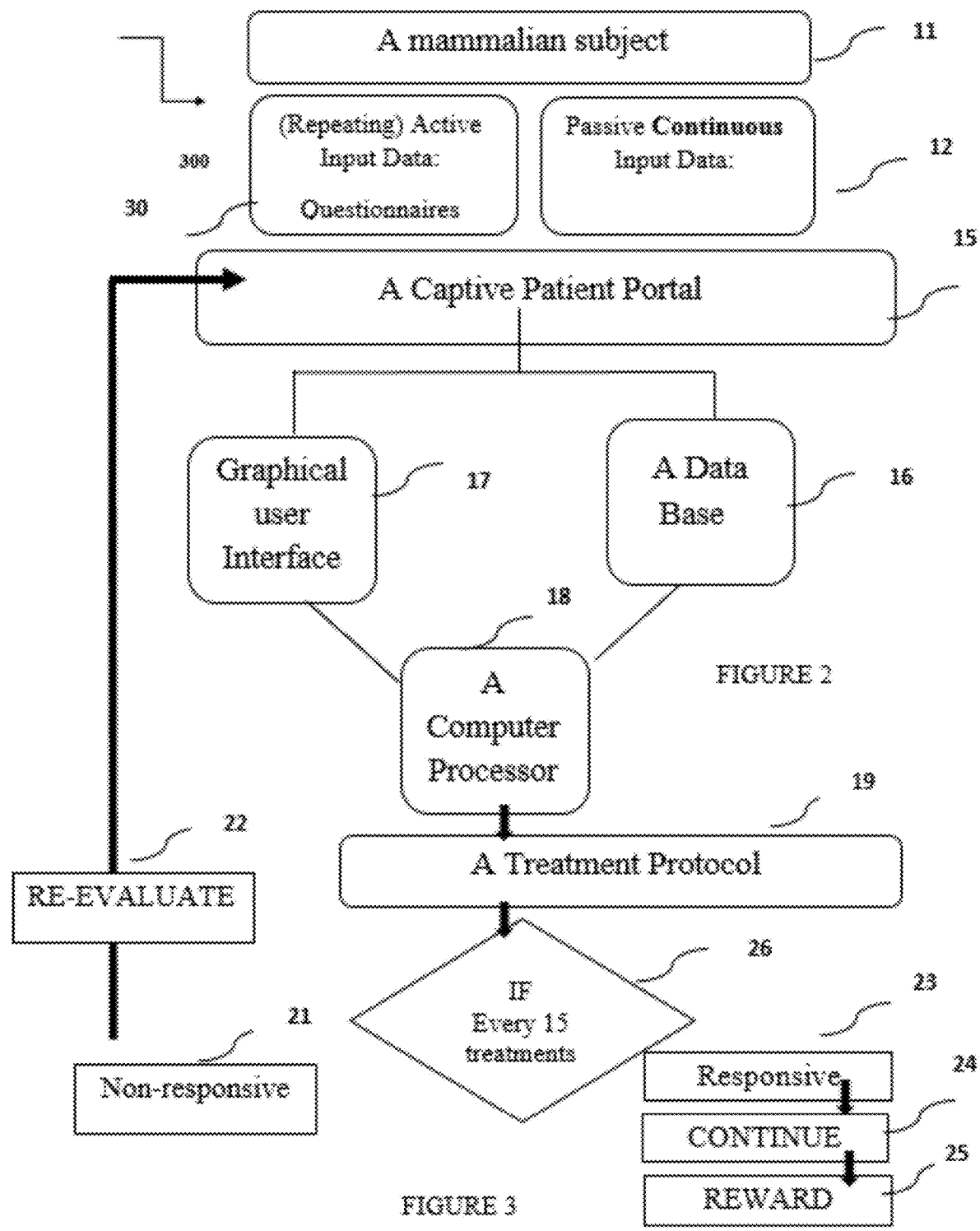
FIG. 3 A method for monitoring mammalian subject, by passive Continuous Input Data combined with Active Input Data, and assessing the need to re-evaluate or continue the current treatment protocol, according to the accumulated Continuous Input Data once every 15 treatments, according to yet another embodiment of the invention.

The Passive Continuous Input Data (12) is accumulated continuously from the subject and include subject' personal information regarding: distance travelled measured by an accelerometer, EEG, HEG, QEEG, velocity, heart rate, blood pressure, body temperature, sleeping time, duration of phone calls, numbers of outgoing and incoming calls and text messages, identification of calls and callers, number of calls, length of calls, number of unique calls, number and duration of visits in restaurants, and fast food sites, sport's sites including swimming pools, gym, electrical activity of the brain, mood parameters, including variability and frequency of mood change, camera photos, location, acquisitions, increased blood pressure, prolonged skin problems, extreme change in appetite, excess gas, frequent dizziness, gastric ulcer, myocardial infarction, inability to work, nightmares, feeling incompetent in all areas, desire to escape everything, apathy, depression or prolonged anger, excessive tiredness, thinking/talking over and over about the same topic, irritability for no apparent reason, daily distress/anxiety, emotional hypersensitivity, loss of sense of humor, cold hands and/or feet, dry mouth, stomach pain, increased sweating, muscle tension, tightening of the jaw/teeth grinding, transient diarrhea, insomnia, tachycardia (increased heart rate) hyperventilation (increased respiratory rate), sudden or transient increased blood pressure, change in appetite, surge of motivation, sudden enthusiasm, sudden urge to start new projects, memory problems, general malaise without specific cause, tingling of the extremities, feeling of constant physical strain, change in appetite, skin problems, increased blood pressure, constant tiredness, gastritis/gastric ulcer, dizziness/feeling as if floating, excessive emotional sensitivity, self-doubt, constant thought about the same topic, constant irritability, decreased libido, frequent diarrhea, sexual difficulties, insomnia, nausea, tics and any combination thereof CPM is a computer processor, which includes an algorithm. The algorithm weighs the percentage of importance to each parameter for each answer. The system provides means for characterizing the type of personality according to combined personal input data (Active Input Data 14, Basic Input Data 13, and Passive Input Data, 12); providing a treatment protocol (19) to the EEG cap (20) according to combined personal input and according to data base (16); assessing the effect of the treatment protocol overtime once every 3 treatments (system 200 of FIG. 2), using Passive Continuous Input Data (12). If (20) the patient is responsive (23), then the treatment protocol continues (24) and the subject is eligible for a reward (25). If (20) the patient is in non-responsive (21), then the treatment protocol is re-evaluated (22), the input data assembled by the Captive Patient Portal (15) is processed again combined with the data base (16) by the Computer Processor (19) to provide a new treatment protocol (19). This process continues until completion of pre-determined set of trainings; assessing the effect of the treatment protocol overtime once every 15 treatments (system 300 of FIG. 3), using Passive Continuous Input Data (12) combined with repeating Active Input Data. If (20) the patient is responsive (23), then the treatment protocol continues (24) and the subject is eligible for a reward (25). If (20) the patient is non-responsive (21), then the treatment protocol is re-evaluated (22), the input data assembled by the Captive Patient Portal (15) is processed again combined with the data base (16) by the Computer Processor (19) to provide a new treatment protocol (19). This process continues until completion of pre-determined set of trainings.

The behavior and daily living actions of the user is scored by Behavioral Scoring Scale (BSS). The BSS is calculated by weighing the values obtained regarding the parameters which are collected by the present invention, mainly parameters collected as Passive Continuous Input Data, over time. These parameters include for example biometric indices, location, sleep clock, heart rate blood pressure, pain, etc. The BSS scores serve as the criteria for determining treatment and duration of treatment and also for the success of the treatment, or the responsiveness of the user/patient.

Treatment recommendations for neurofeedback are determined according to the patient's BSS at For example, it is found that the person is constantly betting, by reporting the location, thus the training protocol will be changed accordingly, to NF of the frontal lobe, aimed at training anxiety.

The user is considered a responder, when the user reaches a pre-determined level BSS.

Figure 12:
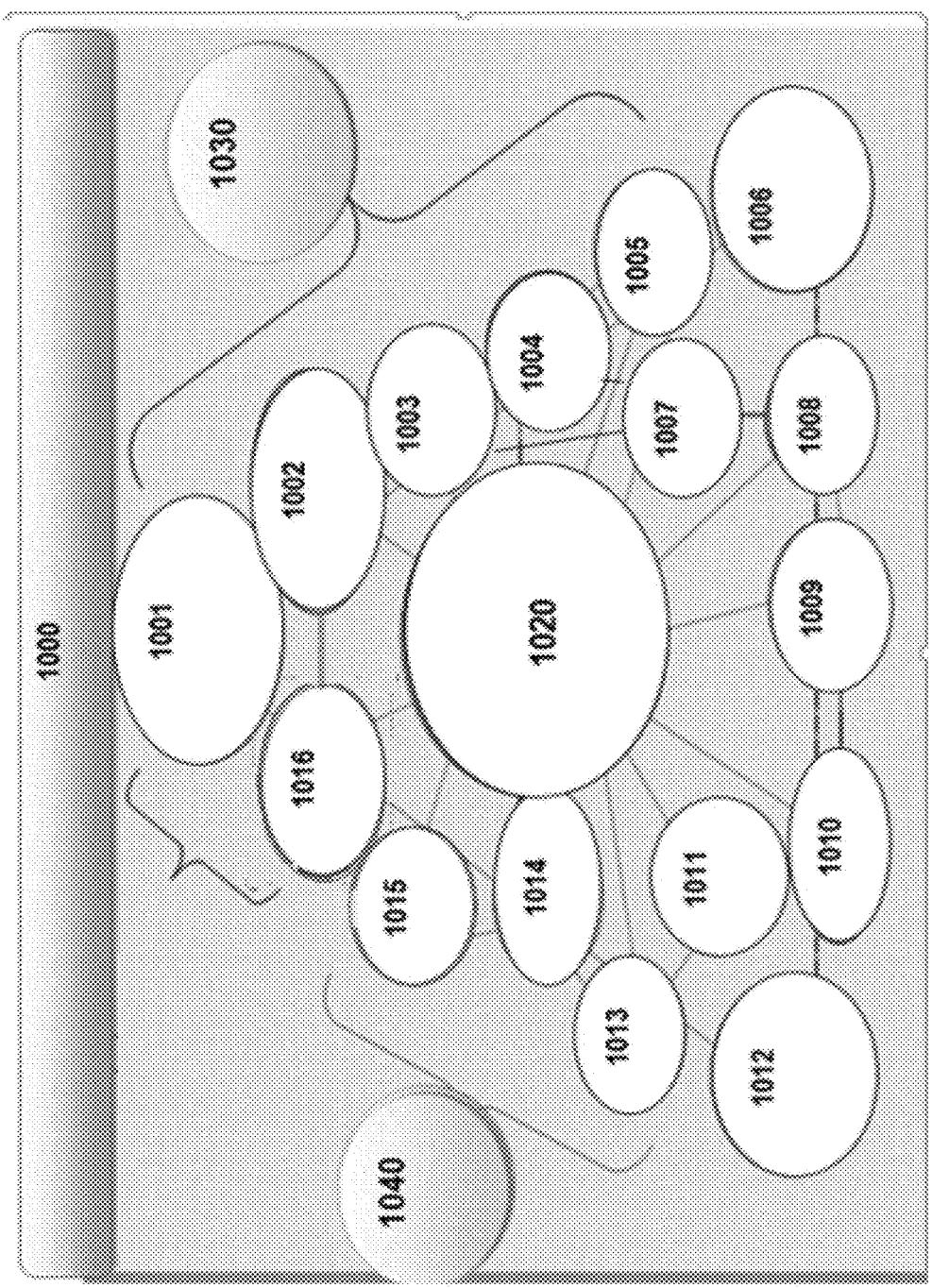
FIG. 12 Holistic view for increased self-control in general and eating habits in particular.

Treatment protocol includes recommendations for the subject in addition to the protocol for neurofeedback (NF) by the EEG cap or a HEG-based NF of a QEEG-based NF. The recommendations include the following, as shown in FIG. 12, in Holistic view for increased self-control in general and eating habits in particular (1000):

1001—Personalized healthy nutrition, 1002—Personalized food supplements, 1003—Personalized physical activity to body size, 1004—Quality sleep, 1005—Joints & skeleton preventive medicine, 1006—Self-confidence & stability, 1007—Reduce pressure and build power, 1008—Body language, 1009—Study & self-development, 1010—Healthy & adaptable sexuality and love life, 1011—Body image & self-esteem, 1012—Order & organization, 1013—Styling. Finding and size shopping, 1014—Economic strength and rights extraction, 1015—Content and personal materialization, 1016—Constant medical monitoring, 1020—Living in better self-control, health and proper nutrition, 1030—Nutrition, medicine prevents illness and pain, and 1040—Personal materialization, welfare, content.

Neurofeedback provides a means of assessing neural response as an independent variable and evaluating its effect on behavior. As such, it can be used as a means of bridging the gap between psychotherapeutic approaches, which combine approaches focused on altering cognitions to facilitate behavior change, and neuromodulation that modulates brain activity by using external invasive or non-invasive procedures or equipment. It also provides an opportunity to improve the understanding and treatment of eating disorders. Neurofeedback is not an exclusive treatment. It is part of a personalized set of recommendations and treatment for eating disorders, uncontrolled and unbalanced eating.

Neurofeedback (NF) is a method that assists subjects to control their brain waves consciously. Neurofeedback is a non-invasive method of direct brain function training and is also a type of biofeedback.

The present invention includes at least three types of NF: EEG-based NF, HEG-based NF and QEEG based NF.

EEG-based NF Electroencephalography (EEG) is a medical imaging technique that reads scalp electrical activity generated by brain structures. The EEG is defined as electrical activity of an alternating type recorded from the scalp surface after being picked up by metal electrodes and conductive media. Electroencephalographic reading is a completely non-invasive procedure that can be applied repeatedly to patients, normal adults, and children with virtually no risk or limitation. When brain cells (neurons) are activated, local current flows are produced. EEG measures mostly the currents that flow during synaptic excitations of the dendrites of many pyramidal neurons in the cerebral cortex. An electroencephalogram (EEG) is a test used to evaluate the electrical activity in the brain. An EEG tracks and records brain wave patterns. Electrodes are attached to the scalp with wires and analyze the electrical impulses in the brain and send signals to a computer that records the results. The electrical impulses in an EEG recording look like wavy lines with peaks and valleys. Any abnormal patterns of these lines may be a sign of seizures or other brain disorders. An EEG is used to detect problems in the electrical activity of the brain that may be associated with certain brain disorders. The measurements given by an EEG are used to confirm or rule out various conditions, including: seizure disorders (such as epilepsy), head injury, encephalitis (inflammation of the brain), brain tumor, encephalopathy (disease that causes brain dysfunction), memory problems, sleep disorders, stroke and dementia. When a patient is in a coma, an EEG may be performed to determine the level of brain activity. This test can also be used to monitor activity during brain surgery. EEG results: Electrical activity in the brain appears in an EEG as a pattern of waves. Different levels of consciousness, like sleeping and waking, have a specific range of frequencies of waves per second that are considered normal. The EEG will show if the frequency of waves or patterns are normal. Abnormal EEG results may be due to: epilepsy or another seizure disorder, abnormal bleeding or hemorrhage, sleep disorder, encephalitis (swelling of the brain), tumor, dead tissue due to a blockage of blood flow, migraines, alcohol or drug abuse, or head injury.

The EEG is recorded during the neurofeedback treatment. Then, its various components are extracted and fed to subjects using online feedback loop in the form of audio, video or their combination. Accordingly, electrophysiological components are separately demonstrated. As an illustration, the power of a signal in a frequency band can be shown by a varying bar graph. During this procedure, the subject becomes aware of the changes occurring during training and will be able to assess his/her progress in order to achieve optimum performance. For instance, the subject tries to improve the brain patterns based on the changes that occur in the sound or movie.

EEG-based NF uses the electrodes placed on the client's scalp of through an EEG cap or an EEG helmet to record and amplify the EEG, or brainwaves and control auditory, visual, and/or tactile feedback which allows learning to take place. This operant learning initiates self-regulation and enhances relaxation, both necessary components of good brain function The electrodes of the NF system, placed on the scalp can record those cortical activities of the brain regions that are close to them. The main brain regions are: frontal, parietal, temporal, occipital, and central areas. The neuro-feedback training is used in the treatment of diseases and disorders; for example ADHD. Evidence suggests that the malfunction of the right frontal lobe, is the cause of attention deficit/hyperactivity disorder (ADHD). The resulting symptoms are inattention, distractibility, hyperactivity, and extreme dispassionateness. Neurofeedback therapy is a rehabilitation approach for its treatment. Its goal is to normalize the behavior without dependence on medications or behavioral therapy.

In traditional neurofeedback, the electrical activity of the brain is monitored using EEG equipment. A more recent development of neurofeedback technology is the Hemoencephalography; HEG-based NF, which is established on a different means of quantifying brain activity. HEM-based NF quantifies brain activity in terms of metabolic activity or metabolic rate in the brain. This field has many implications for brain scans (brain imaging). Metabolism is a cellular process breaks-down glucose by the cells to release the energy that will be available for use by the cell. The process requires oxygen and creates carbon dioxide. A metabolic rate is the rate at which the cell consumes the amount of energy at its disposal. When the brain is engaged in some cognitive task such as calculation, those areas of the brain directly involved in the task use energy at a faster rate than other regions.

HEG-based NF is a specific neurofeedback technique that trains users to consciously regulate cortical blood flow. The practice is based is based on the idea that human beings can consciously alter their brain function through training sessions in which they attempt to change the signal generated by their brain and measured via some neurological feedback mechanism. By so doing, participants increase cerebral blood flow to a specified region of the brain, consequently increasing brain activity and performance on tasks involving that region of the brain], thus a person becomes able to consciously control an unconscious process (blood flow).

Both approaches to HEG, near infrared and passive infrared, are indirect measures of neural activity based on neurovascular coupling. Neurovascular coupling is the mechanism by which cerebral blood flow is matched to metabolic activity. When a region of the cortex is used in a specific cognitive task, neuronal activity in that region increases, consequently increasing local metabolic rate. To keep up with the nutritional and waste removal demands of a higher metabolic rate, cerebral blood flow to the cortical area in use must increase proportionally. Along with the increase in flow, hemoglobin molecules in the blood, which are responsible for the transport and transference of oxygen to tissue throughout the body, must increase the amount of oxygen they deliver to the activated region of the cortex, resulting in a greater local blood oxygenation level. This is also referred to as the haemodynamic response.

Near infrared hemoencephalography measures changes in the local oxygenation level of the blood. Similar to functional magnetic resonance imaging, which uses changes in the magnetic properties of blood resulting from oxygenation to form an image of brain activity, NIR utilizes the changes in blood translucence resulting from oxygenation to generate a signal that can be consciously manipulated in neurofeedback sessions. At the most basic level, NIR hemoencephalography shines alternating red (660 nm) and near infra-red (850 nm) light on a specified area of the brain, usually through the forehead. While the skull is largely translucent to these wavelengths of light, blood is not. The red light is used as a probe, while the infrared light provides a relatively stable baseline for comparison. Photoelectric cells in a spectrophotometer device worn on the forehead measure the amount of each wavelength of light reflected by cerebral blood flow in the activated cortical tissue and send the data to a computer, which then calculates the ratio of red to infrared light and translates it into a visual signal of corresponding to oxygenation level on a graphical interface the patient can see. The key nutrient monitored by NIR is oxygen. In NIR, as the ratio of oxygenated hemoglobin ($HbO_2$) to deoxygenated hemoglobin (Hb) increases, the blood becomes less and less translucent and scatters more of the red light, instead of absorbing it. In contrast, the amount of infrared light scattered by the blood is largely impermeable to changes in the oxygenation level of hemoglobin Passive infrared (PIR) Passive infrared HEG is a combination of the classic hemoencephalography principles and a technique known as thermoscopy. PIR uses a sensor similar to the NIR sensor to detect light from a narrow band of the infrared spectrum that corresponds to the amount of heat being generated by an active brain region, as well as the local blood oxygenation level. The heat detected by PIR is proportional to the amount of sugar being burned to maintain the increased metabolic rate necessary to fuel elevated neuronal activity. PIR has a poorer resolution than NIR and this treatment typically focuses on more global increases in cerebral blood flow.

Adjunct therapy The biofeedback system of the current invention is not only a single therapy, the system is used as a tool for the complementary treatment adjunct to conventional medicine, cannabis, surgery and medical procedures. The goal of the treatment is creating motional balance and improving self-performance in order to deal with impulses and challenges, as well as developing self-awareness of unwanted and uncontrolled eating behaviors while developing strengths by improving management functions and reducing ego depletion. This system provides a holistic approach for treatment. The system creates a support for treatment, by characterization using a questionnaire and/or experiential neurofeedback training, and especially in recommendations based on an agenda of ego depletion. The NF system can serve as an adjunct treatment for bariatric surgery, for pharmacological interventions, as a supplement to existing treatments such as, psychopharmacologic treatment, any diet regimens, weight control, and treatments for obstructive sleep apnea.

Cannabis: Cannabis-based medications have been a topic of intense study since the endogenous cannabinoid system was discovered two decades ago. Cannabis preparations exert numerous therapeutic effects. They have antispastic, analgesic, antiemetic, neuroprotective, and anti-inflammatory actions, and are effective against certain psychiatric diseases.

Use of cannabis can have a variety of psychological effects. It generally causes a sense of heightened mood or "high." This can lead to decreased anxiety and increased social interaction. Additionally, there has been a recent increase in prescription of medicinal cannabis among minors and more demand by parents seeking an alternative route to allopathic medications. There have been some initial positive results in the use of cannabis in treating different disorders in children including cancer, autism, and attention deficit hyperactivity disorder, see Behere, A. et al (2017). *Cannabis: Does it have a medicinal value? Indian Journal of Psychiatry,* 59(3), 262-263, incorporated herein as a reference.

Furthermore, cannabidiol (CBD), the main non-psychotropic constituent of the *Cannabis sativa* plant showing broad therapeutic potential in various psychiatric diseases. Studies in humans demonstrate the promise of CBD for treating anxiety and preclinical studies in rodents are elucidating the pharmacological mechanisms underlying its acute anxiolytic effects. These mechanisms include potentiation of serotonin (5-HT) transmission via 5-HT1A receptor (5-HT1AR) activation and elevation of endocannabinoid levels via inhibition of their metabolism and re-uptake, which indirectly facilitates cannabinoid receptor type1 (CB1R) activation.

CBD reduces learned fear expression, disrupts fear memory reconsolidation, and facilitates fear extinction. As well as reducing anxiety in behavioral tests of unconditioned fear, emerging evidence indicates that CBD regulates fear learning and memory in paradigms that are translationally relevant to diseases such as phobias and PTSD, along with their psychological treatments, see Jurkus, R., et al (2016). Cannabidiol Regulation of Learned Fear: Implications for Treating Anxiety-Related Disorders. *Frontiers in Pharmacology*, 7, 454, incorporated herein as a reference.

The training takes is also by virtual reality (VR) programs so that it will be experienced for children and adults to persevere in training and not abandon training, Virtual reality has a very significant additional force, which is the ability to integrate content into practice, and to produce virtual reality that will give value to the trainee, thus teaching the trainee via a practical experience in virtual reality to improve this/her functional deficiencies detected by the questionnaire. For example: the trainee's questionnaire reported that he/she slept a little and got tired. Virtual reality training with neurofeedback will be a reality in which he/she will initiate a process of "sleep hygiene" in which he/she functions before bedtime, i.e., setting an alarm clock that is not on a mobile phone, operating a night light, sleeping at a reasonable time, reading a book.

Example 1: AD(H)D Classification Questionnaire

Part A of the questionnaire comprises of 12 questions Part A, includes 12 questions, which are offered to any user. After the user answers all 12 questions, the user is characterized for the three AD(H)D classifications types: Frontal, Temporal, and Parietal.

The questions are as follows:
1. The food serves me to dull thoughts or feelings connected to my body
2. I crave food when I am bored, angry or sad
3. Eating comforts me
4. I find I ate more than I thought
5. I find it difficult to begin and persist in deciding on proper nutrition
6. I eat without thinking
7. I eat regardless of my level of appetite or satiety
8. Being with someone who eats makes me feel hungry
9. When I'm hungry my stomach is like a bottomless hole
10. I have an urge to finish the entire package that remains
11. I eat even though I know it will have results
12. To what extent do you worry about your weight?

The algorithm for Part A questionnaire is shown in the following paragraph named Algorithm integration, Part B: Health Promoting Questionnaire After completing answering the questions of Part A, the user answers the questions of Part B. The questions or Part B are suited for each user according to the AD(H)D classification of the user, as determined by result of Part A questionnaire and the algorithm. Part B, health promoting questionnaire has 3 different formats, according to the personality type defined in Part A. Part B is therefore a questionnaire, adjusted to the type of the user.

In part B, each user receives several statements. The user then marks each statement in values from 1-6, while values 1 reflects the fact that the statement does not characterize this user, while value 6 reflects the fact that this statement characterize best the user.

These statements are associated with the relevant brain area.

Every question in Par b the questionnaire has an expression of a statement such as worry, anxiety, anxiety, obsessiveness, etc.

The statements are listed in Table 1.

Table 1 Describes the Statements and their Relation to AD(H)D Classifications

TABLE 2

Health promoting questionnaire statements

| AD(H)D classification/statements | The statements used for preparation of the user's report |
|---|---|
| FRONTAL (Managerial) | |
| Do not stop thinking about food during the day | Obsessive thinking about eating during the day. |
| I eat without thinking | Impulsivity: Eating without thought. |
| Difficulty facing the temptations | Impulsivity: Difficulty facing temptations |
| I eat whatever I want and do not think about health | Difficulty in making decisions: considerations of health food choices are not taken into account |
| I have no agenda when I eat | Difficulty in making planning and organization decisions: There is no fixed order and hours for meals. |
| I do not eat all day and then I attack the food | Difficulty in planning and organizing decisions: Unorganized eating that leads to eating large volumes in one meal unit. |
| I find it difficult to begin and persist in deciding on proper nutrition | Difficulty in making decisions, procrastination: Difficulty initiating a process that requires multiple mental resources. |
| I eat even though I know it will have physical/emotional/interpersonal/ personality results | Difficulty in making planning and organizing decisions: eating despite the knowledge that this will have consequences. |

TABLE 2-continued

Health promoting questionnaire statements

| AD(H)D classification/statements | The statements used for preparation of the user's report |
|---|---|
| I find I've eaten more than I thought | Problems with attention and memory: the discovery of a large amount is planned or calculated. |
| TEMPORAL (regulation) | |
| I worry about what my weight will be | Worries: Concerned about weight and its consequences |
| Because I worry about my weight and health, I prefer not to do anything | Concerns: Concern for weight and health leads to inactivity. |
| I say to myself, "I wish I had eaten" | Intimidating internal speech: "I say to myself that I ate." |
| It's hard with new foods I do not know | Hypersensitivity: Difficulty with unfamiliar new foods. , Reluctance to experiment |
| I am very disturbed by the smells/textures of certain foods | Sensory regulation: It is difficult to vary nutrition due to disturbance of smells/textures of various foods, which prevents dietary diversity. |
| I also eat that I'm not hungry | Lack of awareness of appetite: uncontrolled eating behavior for physiological purposes. |
| I eat only when my stomach is already "stuck to my back" | Lack of awareness of appetite: Eating unconsciously and adapted to the needs of the body. |
| I'm disgusted with certain foods | Hypersensitivity: feeling disgusted with certain foods |
| I eat and I do not care what they say | Difficulty identifying social cues: Eating without reference to social reactions |
| PARIETAL (emotional) | |
| The food serves me to dull thoughts or feelings connected to my body | Pain: dulling thoughts and physical sensations with food. |
| I am afraid of what will happen to me if I continue with an uncontrolled diet | Anxiety: I am afraid of what will happen if I continue to conduct an uncontrolled diet. |
| I crave food when I am bored, angry or sad | Calm: Conditions such as boredom, anger, sadness are triggers for eating. |
| I have an urge to finish eating the whole package that remains | Addiction: There is an impulse that motivates me to eat of any food package. |
| It's hard for me to control eating | Addiction: Difficulty in controlling eating |
| Eating comforts me | Emotional: Eating makes you feel comforted. |
| When I get annoyed I go to eat | Emotional: A response to arousal (nerves) leads to an eating response. |
| I did not have the peace of mind to fall asleep until I did not eat | Anxiety: Finding peace of mind in the act of eating. |
| I'm not comfortable with people measuring me | Body image: External measurement of strangers towards me causes me discomfort. |

Table 3: Health Promoting Questionnaire—Characterization for User Report

TABLE 3A

FRONTAL

| A statement in the questionnaire | Characterization sent to USER REPORT |
|---|---|
| 1. Do not stop thinking about food during the day | 1. Obsession: continues thinking about eating during the day. |
| 2. I eat without thinking | 2. impulsiveness: Eating without thought. |
| 3. Difficulty facing the temptations | 3. impulsiveness: Difficulty facing temptations |
| 4. I eat whatever I want and do not think about health | 4. Difficulty in making decisions: Considerations healthy food choices is not taken into account |
| 5. I have no agenda when I eat | 5. Difficulty in making planning and organization decisions: There is no fixed order and hours for meals. |
| 6. I do not eat all day and then I attack the food | 6. Difficulty in making planning and organization decisions: An uncontrolled eating leads to eating large explosives unit h s one meal. |
| 7. I find it difficult to begin and persist in deciding on proper nutrition | 7. Difficulty in making decisions, procrastination: Difficulty initiating a process that requires multiple mental resources. |
| 8. I eat even though I know it will have physical/emotional/interpersonal/personality results | 8. Difficulty in making planning and organizing decisions: eating despite the knowledge that this will have consequences. |
| 9. I am very disturbed by the smells/textures of certain foods | 9. Sensory Integration: It is difficult to vary nutrition due to disturbance of smells/textures of various foods, which prevents dietary diversity. |
| 10. I do not make food for me to leave the house | 10. Difficulty in planning and organizing: Lack of organization in the order of meals when leaving home. |

TABLE 3A-continued

FRONTAL

| A statement in the questionnaire | Characterization sent to USER REPORT |
|---|---|
| 11. I find I've eaten more than I thought | 11. Problems with attention and memory: the discovery of a large amount is planned or calculated. |

TABLE 3B

TEMPORAL

| A statement in the questionnaire | Characterization sent to USER REPORT |
|---|---|
| 1. I worry about what my weight will be | Worries: Concerned about weight and its consequences |
| 2. Because I worry about my weight and health, I prefer not to do anything | Concerns: Concern for weight and health leads to inactivity. |
| 3. I say to myself, "I wish I had eaten" | Intimidating internal speech: "I say to myself that I ate." |
| 4. It's hard with new foods I do not know | Hypersensitivity: Difficulty with unfamiliar new foods., Reluctance to experiment |
| 5. I worry about what my weight will be | Worries: Troubled by my future weight |
| 6. I also eat that I'm not hungry physiological purposes. | Lack of awareness of appetite: uncontrolled eating behavior for |
| 7. I eat only when my stomach is already "stuck to my back" | Lack of awareness of appetite: Eating unconsciously and adapted to the needs of the body. |
| 8. I'm disgusted with certain foods | Hypersensitivity: feeling disgusted with certain foods |
| 9. I eat and I do not care what they say | Difficulty identifying social cues: Eating without reference to social reactions |

TABLE 3C

PARIETAL

| A sentence in the questionnaire | Characterization sent to USER REPORT |
|---|---|
| 1. The food serves me to dull thoughts or feelings connected to my body | Pain: dulling thoughts and physical sensations with food. |
| 2. I am afraid of what will happen to me if I continue with an uncontrolled diet | Anxiety: I am afraid of what will happen if I continue to conduct an uncontrolled diet. |
| 3. I crave food when I am bored, angry or sad | Calm: Conditions such as boredom, anger, sadness are triggers for eating. |
| 4. I have an urge to finish eating the whole package that remains | Addiction: There is an impulse that motivates me to eat the whole package |
| 5. It's hard for me to control eating | Addiction: Difficulty in controlling eating |
| 6. Eating comforts me | Emotional: Eating makes you feel comforted |
| 7. When I get annoyed I go to eat | Emotional: A response to arousal (nerves) leads to an eating response. |
| 8., There was no me peace of mind to sleep until he ate | Anxiety: Finding peace of mind in the act of eating. |
| 9. I'm not comfortable with people measuring me | Body image: External measurement of strangers towards me causes me discomfort. |

TABLE 3C-continued

PARIETAL

| A sentence in the questionnaire | Characterization sent to USER REPORT |
|---|---|
| 10. The food serves me to dull thoughts or feelings connected to my body | Body image: dulling thoughts and feelings through food |

Algorithm Integration

Part A: AD(H)D classification questionnaire is presented to the user by phone application, by an interview (in clinics or home), by computer . . . etc.

The user receives a questionnaire of 12 questions in which he must choose between 1 and 6, as well as demographic questions about age, weight, height, gender and economic status.

Two of the questions are general questions to provide background for the therapist.

The other 10 questions fall into three categories:
FRONTAL Management;
TEMPORAL Regulation; and
PARIETAL Emotional.

Each user will be reported regarding the AD(H)D classification to which the user belongs. The user also receives the value in each personality type, and report which state whether the user received a value higher than the 75 percentile/25 percent lower than the 25 percent median/between the median and the 75 percent.

How it is done: Three variables (frontal, temporal, and parietal) are created, and each variable t includes the average number of responses to each category.

A variable called "your type" is created in which the user is presented to the subject (frontal/temporal/parietal) in which the subject is given the highest value.

Figure 18:
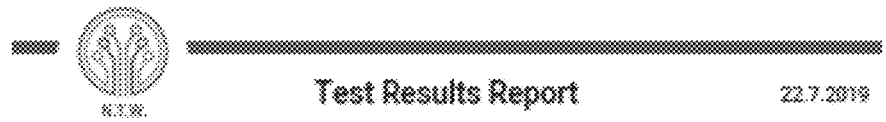
FIG. 18 Output report presented to subject user.
Figure 18:
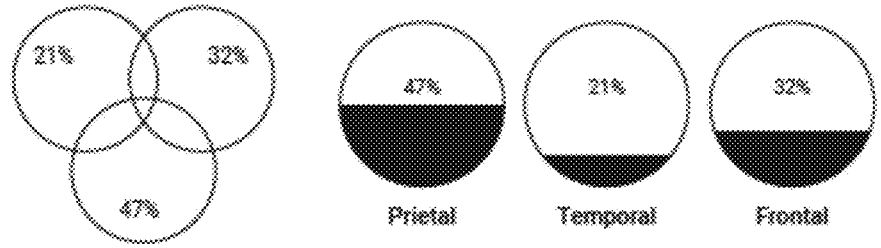

According to the age group to which the user belongs (10-24, 25-44, 45-65), the application chooses the appropriate norm scales. The subject receives a USER REPORT presented by a ruler divided into four parts (25-50%, 25-50%, 50-75%, higher than 75%). For example see FIG. 18.

Example: The subject is 18 years old, and received in the "frontal" AD(H)D classification an average score of 4.75 out of the three questions belonging to this category;

received in the "temporal" AD(H)D classification an average score of 2.67 out of the three questions belonging to this category; and received 5.25 in the "parietal" AD(H)D classification an average score of the three questions belonging to this category The user receives a result: "your Personality type is "Parietal", Additionally, the user receives 3 such rulers, which reflect the user's score/values relative to the normal values of the age group in each category (the following are the normal values are depicted in Table 2):

Table 4:

TABLE 4A

Normal values/scores for Algorithm calculation for Ages 10-24

|  | Median Percentile 75 | Median | Percentile 25 |
|---|---|---|---|
| FRONTAL | 5.33 | 4.33 | 3.33 |
| TEMPORAL | 4.75 | 3.75 | 3 |
| PARIETAL | 5 | 4.33 | 3 |

TABLE 4B

Normal values/scores for Algorithm
calculation for Ages 25-44

|  | Median Percentile 75 | Median | Percentile 25 |
|---|---|---|---|
| FRONTAL | 4.67 | 4 | 3 |
| TEMPORAL | 4.25 | 3.25 | 2.5 |
| PARIETAL | 4.67 | 3.67 | 2.67 |

TABLE 4C

Normal values/scores for Algorithm calculation for Ages 45-65

|  | Median Percentile75 | Median | Percentile 25 |
|---|---|---|---|
| FRONTAL | 5 | 4 | 3 |
| TEMPORAL | 4.25 | 3.25 | 2.25 |
| PARIETAL | 4.67 | 3.67 | 2.67 |

Part B:

The user values statements which are were adjusted to the AD(H)D classification of the user.

The algorithm sums the answers' values, and the user receives a user report which comprises, inter alia, the characterization, which correlates to the statements which received the highest values. (see Table 4A-C in the previous paragraph).

Part C—QEEG Test which is Characterized as One of the Three Types (or a Combination of Two Types If the same AD(H)D classification appear in both the questionnaire and QEEG. This type will appear in the final USER REPORT.

If In the questionnaire, type A went out and in QEEG type B emerged. In the final report the two types would appear in the final USER REPORT.

Partial overlap: In QEEG there were 2 type AD(H)D classifications and only one of them came out on the questionnaire. A two-type program will be offered. in the final USER REPORT For each type of disorder an algorithm will be built according to the research data that will be used for this purpose. In the case of obesity, for example, the treatment protocol established by the QEEG professionals was compared to the protocol they determined according to the questionnaire, and by comparing them, the algorithm was developed according to which (this paragraph can be left because it is intended only to demonstrate)

Example 3: Clinical Study

Part I of the Study: Development of a Diagnostic Tool Assessment Tool

Part A of the present study was designed to develop a tool that combines a questionnaire with subjects and a QEEG test as part of a computerized assessment of subjects (in the first stage of assessment of readiness for weight loss treatments). Based on the evolving knowledge in neuroscience, and in keeping with the knowledge about the common factors in an uncontrolled diet, three main brain sources relevant to the assessment of uncontrolled eating behavior were identified:

The frontal region—responsible for management functions—can explain uncontrolled behaviors associated with attention, planning and organization disorders, in making orderly and balanced decisions.

The parietal region—associated with resting the brain and emotional challenges such as anxiety or traumas—can explain emotional eating.

The right temporal region—which is responsible, among other things, for regulation, ויסות can explain eating that is not regulated in line with internal and external cues.

The stages of developing the questionnaire:

Stage1: A pilot questionnaire was constructed with 60 statements on a 6-point Likert scale. The statements are based on a number of accepted obesity questionnaires. The pilot questionnaire was distributed to 150 people. Following statistical analysis, the statements were revealed and the questionnaire was distributed in its shortened version to 1,300 people. It was found that the questionnaire in its final version can clearly identify a "dominant type" of the focus of difficulty in the subject: frontal management, parity, and temporal regulation. The following is the final "sample type" model(see FIG. 13)

Figure 13:
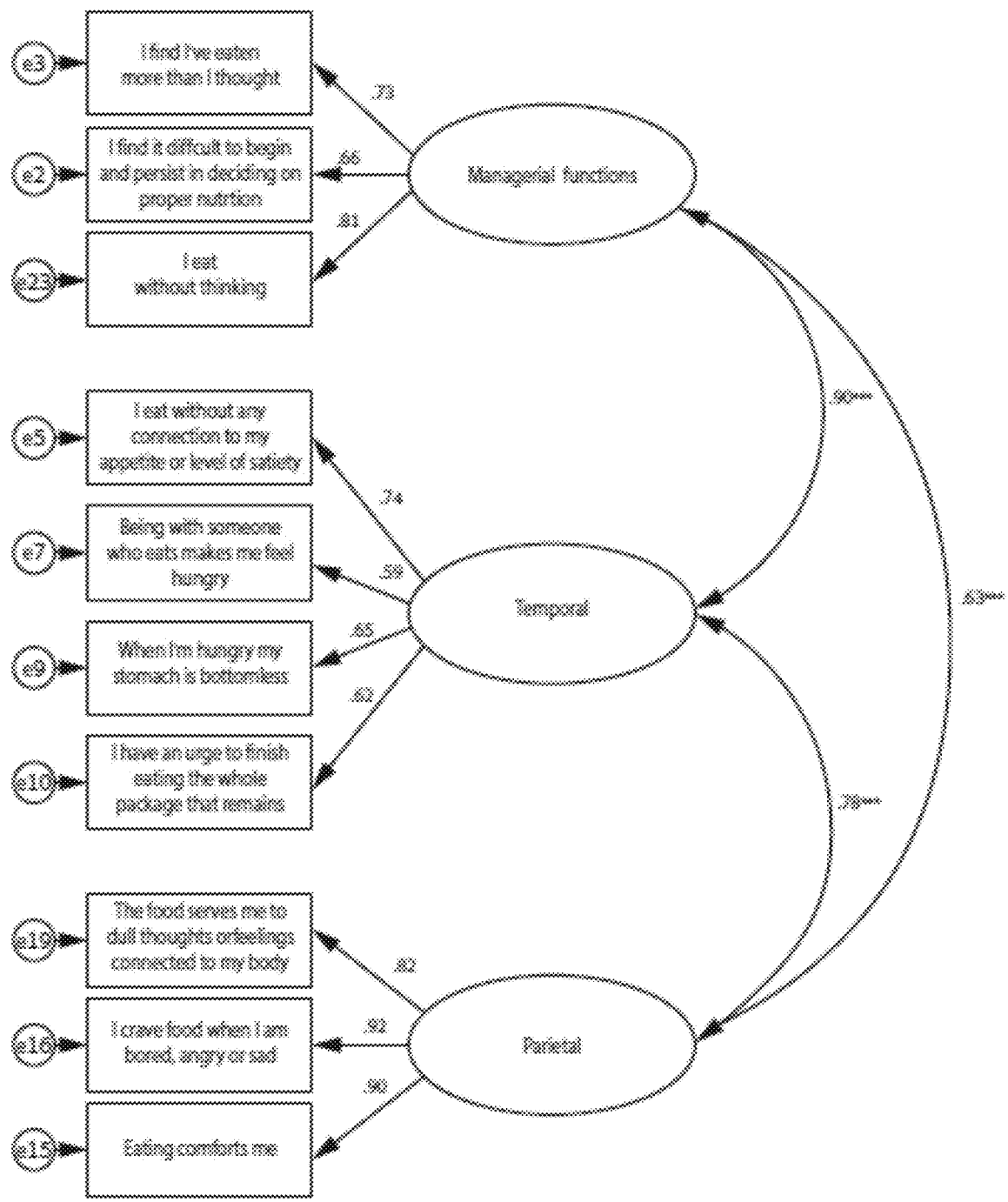
FIG. 13 A statistical analysis of the model using AMOS program.

The model: FIG. 13 depicts a statistical analysis of the model using AMOS program. The results reveled the following findings:

Chi Square=49.867, (DF=32), p=0/023.
Chi/df=1.558, RMSEA=0.059, SRMR=0.0388, TLI=0.969, NFI=0.942, CFI=0.978.

The results of the AMOS program showed that the items in the questionnaire and the variable (parietal/frontal/temporal) to which they belong have a positive correlation. Statistical measures used to test the quality of the model indicate that the model is statistically good.

The model is statistically good because at least three of the model's quality measures meet the relevant criteria. For example, RMSEA should be less than 0.6, in which case it is 0.059. SRMR should also be less than 0.9 in combination with one of the other CFI TLI indices, which should be greater than 0.95, which is in this model (SRMR=0.0388, TLI=0.969, CFI=0.978). In addition to NFI, which is the ratio of the difference between the maximum possible squared (maximum independence) and the squared animal, to the maximum possible squared, you should be above 0.9 and in this case NFI=0.942. Therefore, this model is a good model that meets the statistical requirements for this purpose. In addition, it is desirable that the squared indicator be not significant and approach 0. In this model, the level of significance of a square animal (Chi square=49.86, DF=32) is 0.023.

Part B: For a group of 50 subjects, two parts of the diagnosis were performed: a diagnosis using the type questionnaire and a diagnosis by examining brain activity using QEEG in the three relevant areas: frontal, parietal, temporal.

In the next stage, a comparison was made between the results of the diagnosis (treatment recommendations) according to the type questionnaire versus the results according to the QEEG test. It was decided that each recommendation would include two focal points of difficulty, given that 60.8% of the subjects had more than one type of focal point (frontal/parietal/temporal).

A comparison of the results of the diagnosis with these two tools enabled us to learn about how to simplify and streamline the diagnostic process. Only 6 out of 50 subjects did not agree, ie, in 88% of cases, there was agreement between recommendations according to QEEG and recommendations of the therapist. In 10 out of 50 subjects, the algorithm would be wrong if it had only the questionnaire, ie, 80% could rely on the questionnaire alone [recommending two foci of difficulty]. The characteristics of the cases in which the questionnaire is not suitable for prediction in it, and where it is necessary to combine the QEEG test with the updated algorithm.

This finding is a breakthrough in simplifying and streamlining the evaluation of preparedness for weight loss treatments. As a result of this finding, a simple and effective computerized system for evaluation of readiness to weight loss treatments, based on a short and convenient questionnaire supported by QEEG testing, can be constructed. The fact that the new tool (questionnaire) provides results close to those of familiar tool (QEEG) results, reinforces the possibility of using the questionnaire as a primary tool for evaluating preparedness. It should be noted that in some cases, listed in a separate document, the questionnaire is less suitable for prediction by itself, and it is necessary to combine it with a QEEG test.

Part II of the Study: Brain Training (Neurofeedback) for the Treatment of Uncontrolled Diet and Increased Readiness for Slimming The study hypothesis: The scores of the indicators of uncontrolled eating behavior are expected to decline following a series of neurofeedback training.

Participants: In this part of the study, 12 subjects in the experimental group and 34 in the control group participated.

The following are demographic characteristics of the participants:

In the experimental group, 83.3% were women, with a broad age range (67-13 years) with an average age of 46.5 (SD=13.5). In the control group, 67.6% were women, with a broad age range (12-70 years) with mean age of 43.7 (SD=14.97).

Most of the participants in the study (80%) did not have a normal BMI. 10.9% underweight, 21.7% normal weight, 26.1% overweight, 17.4% obesity level 1, 10.9% obesity level 2, 13% obesity level 3.

Research tools a. An AD(H)D classification questionnaire, with an emphasis on managerial functions including impulsivity, procrastination, ambition questionnaire, eating and activity and sleep habits questionnaire, which its development was described in Part A above, was transferred prior to the training series and after the training series to both the experimental group and the control group.

b. readiness questionnaire for change in two versions was transferred to the experimental group before and after the training series: one version to be completed by the subject and a second version to be completed by a relative about the subject.

Research Process: The control group received no treatment.

Research procedure in the experimental group: Using an algorithm that weights questionnaire data and QEEG data (as mentioned in Part A of the above study), a protocol for a Neurofeedback training series was constructed for each participant in the experimental group. The two locations selected for training were the two locations identified by the algorithm as the highest of the three options: frontal, temporal, and parietal. Each participant practiced a total of 30 training sessions twice a week for 30 minutes per session, 15 minutes in one place and 15 minutes in the second.

The training included watching videos in the BioExplorer program for neurofeedback training and using a NeurobitOptima2 measuring instrument.

Results The study hypothesis was strongly confirmed: the scores of uncontrolled eating behavior scores declined significantly following a series of neurofeedback training in the experimental group rather than in the control group.

AD(H)D classification questionnaire: To test the hypothesis that there was a difference in the level of uncontrolled eating behavior before and after the neurofeedback training series, t-tests were performed for paired samples and significant differences were found (p<0.01) indicating that the level of uncontrolled eating behavior declined following a series of neurofeedback training in the experimental group, (Frontal, temporal, parietal) and the general average. In the control group there were no significant changes during this period. In addition, a t-test was conducted for independent samples to compare the difference in the level of uncontrolled eating behavior at both time points, before and after the experiment, between the experimental group and the control group. A significant difference was found. The results in Tables 5-7.

In other words, we can see a decrease in the rating of the uncontrolled eating behavior (in the statements detailed in the above sample questionnaire) by comparing the two time points (pre-post-experiment) in the experimental group rather than in the control group, and the difference in the reported change is statistically significant. In general, the rating of the uncontrolled behavior of the experimental participants was lower at the end of the experiment than in its initial phase, ie, a decline in the rating of uncontrolled eating behavior.

Examples of statements describing uncontrolled eating behavior (from the sample questionnaire): "I find that I ate more than I thought," "the food is used to dull thoughts or feelings that are related to my body," etc. In addition, participants in the experimental group rated at a lower level than reported at the beginning of the experiment behaviors in each category in its own right: a reduction in the experimental group only before and after the experiment in rating behaviors in the parietal class, a decrease in the experimental group only after the experiment in the frontal class—After the experiment in the ranking of behaviors in the temporal category.

2. A Readiness for Change Questionnaire

A. In a Version to be Filled by a Relative about the Subject

Figure 14:
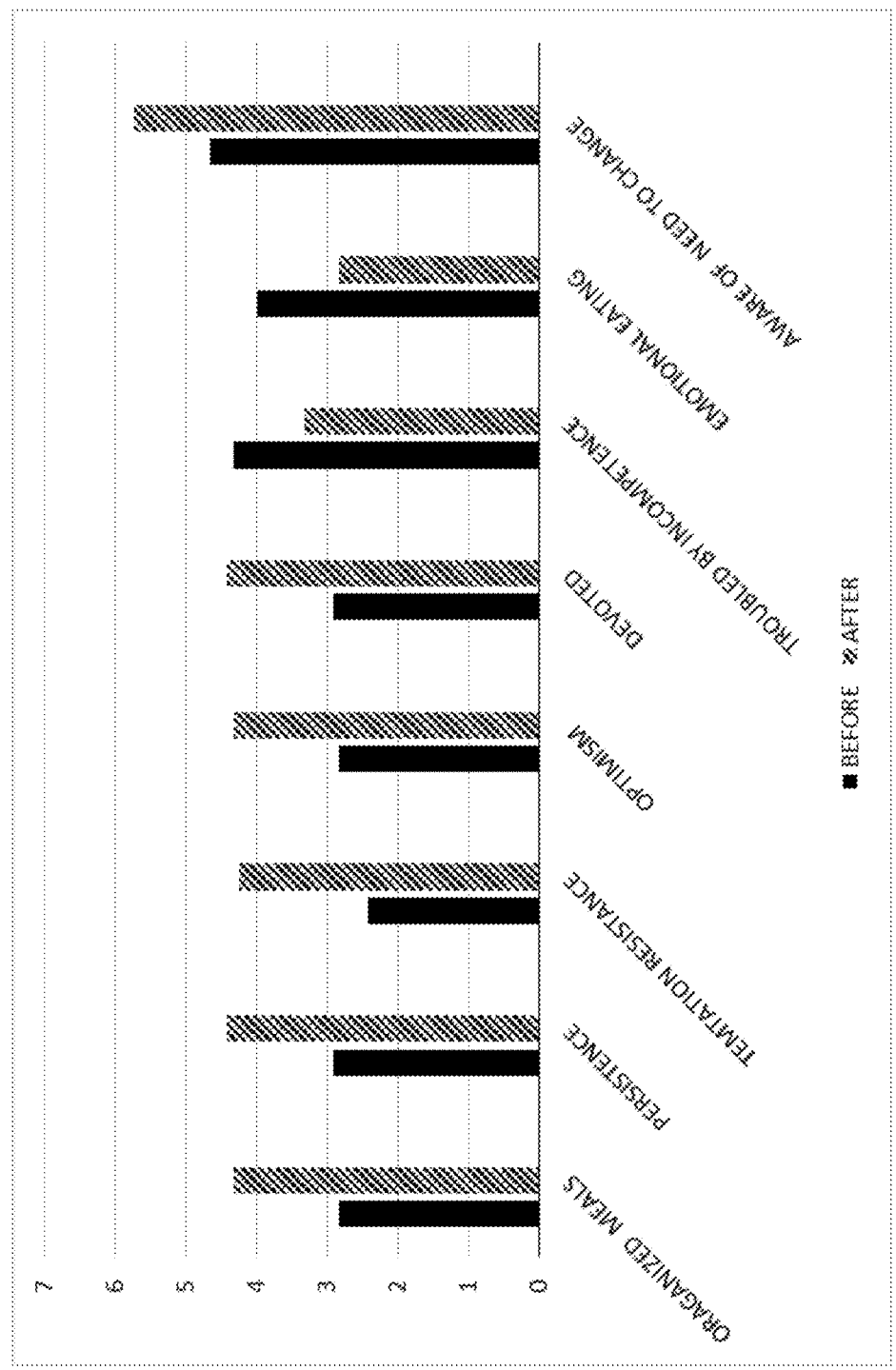
FIG. 14 Results of clinical study; perceptions and statements of relatives of the experimental group users, significant differences before versus after a series of neurofeedback training ($p<0.05$)
Figure 15:
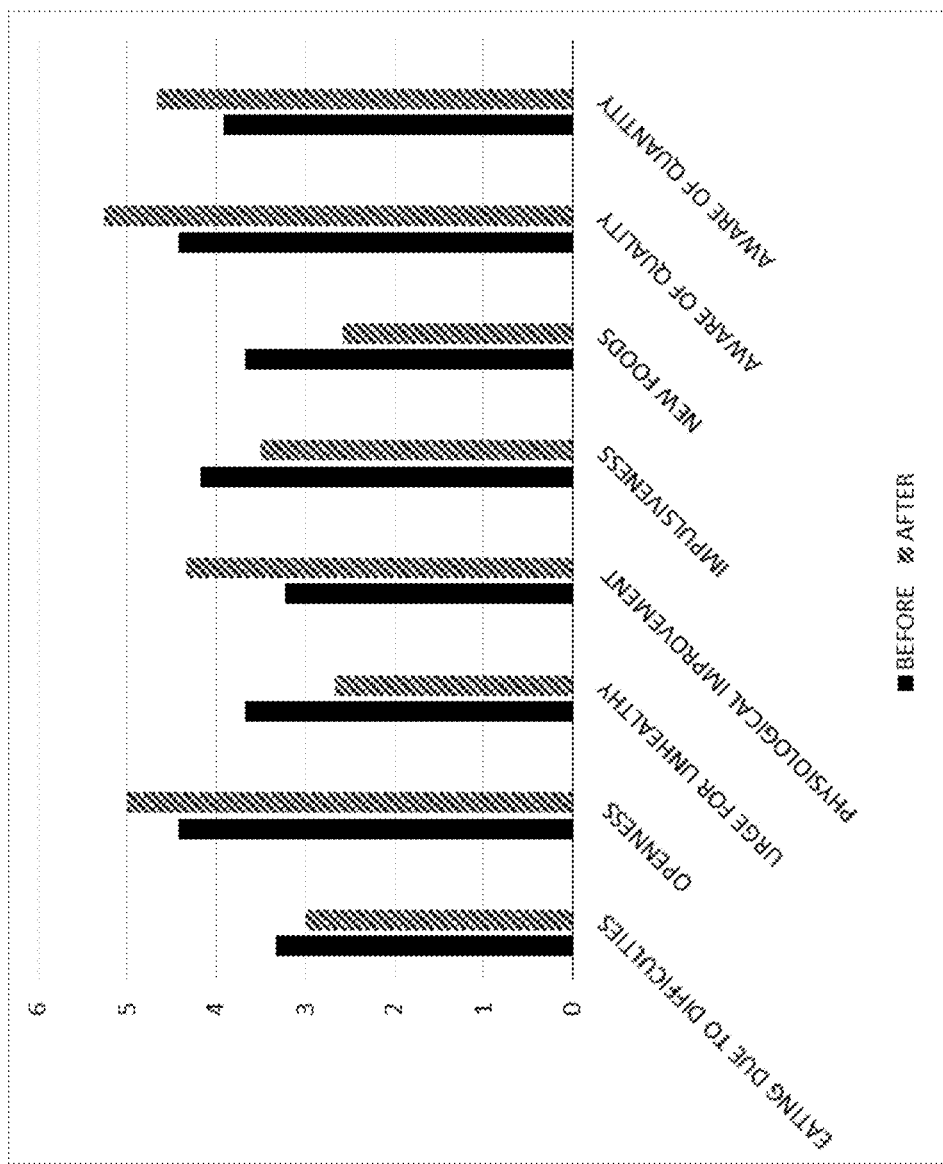
FIG. 15 Results of clinical study; perceptions and statements of relatives of the experimental group users, non-significant differences before versus after a series of neurofeedback training ($p>0.05$)

In the t-test for paired samples, there was no significant difference in the perception of family members before and after training in health-conscious awareness (to what extent the subject is open to supportive messages for a healthy lifestyle, aware of the quality/quantity of foods that I can eat) As shown in FIG. 14. However, after the training series, there is a significant increase in their perception of the patient's level of optimism, dedication and persistence, sense of ability and organization, as can be seen in FIG. 15.

TABLE 5

Changes in uncontrolled eating behavior measured in a sample questionnaire at the beginning and end of the experiment

| CONTROL | | | EXPERIMENT | | | |
|---|---|---|---|---|---|---|
| STATISTICS | AFTER | BEFORE | STATISTICS | AFTER | BEFORE | TYPE |
| t(33) = −0.18 ns | M = 2.89 SD = 1.18 | M = 2.87 SD = 1.16 | t(11) = 3.34 p < 0.01 | M = 2.54 SD = 1.05 | M = 3.47 SD = 1.17 | FRONTAL |
| t(33) = 0.22 ns | M = 3.14 SD = 1.17 | M = 3.17 SD = 1.17 | t(11) = 4.32 p < 0.01 | M = 3.5 SD = 1.43 | M = 4.28 SD = 1.07 | TEMPORAL |
| t(33) = −0.89 ns | M = 2.95 SD = 1.04 | M = 2.84 SD = 1.15 | t(11) = 3.89 p < 0.01 | M = 2.83 SD = 0.93 | M = 3.72 SD = 1.19 | PARIETAL |
| t(33) = −0.43 ns | M = 2.99 SD = 0.98 | M = 2.96 SD = 0.99 | t(11) = 4.9 p < 0.01 | M = 2.96 SD = 0.94 | M = 3.82 SD = 0.97 | AVERAGE |

TABLE 6

Comparison between the experimental group and the control group in the gap measured in the pre-post-experimental type questionnaire

| STATISTICS | CONTROL | EXPERIMENT | |
|---|---|---|---|
| t(44) = 3.58 p < 0.01 | M = −0.02 SD = 0.72 | M = 0.92 SD = 0.96 | BEFORE-AFTER GAP-FRONTAL |
| t(44) = 2.93 p < 0.01 | M = 0.03 SD = 0.8 | M = 0.78 SD = 0.62 | BEFORE-AFTER GAP-TEMPORAL |
| t(44) = 4.04 p < 0.01 | M = −0.11 SD = 0.71 | M = 0.88 SD = 0.79 | BEFORE-AFTER GAP-PARIETAL |

B. In the Version to be Filled by the Subject

Figure 16:
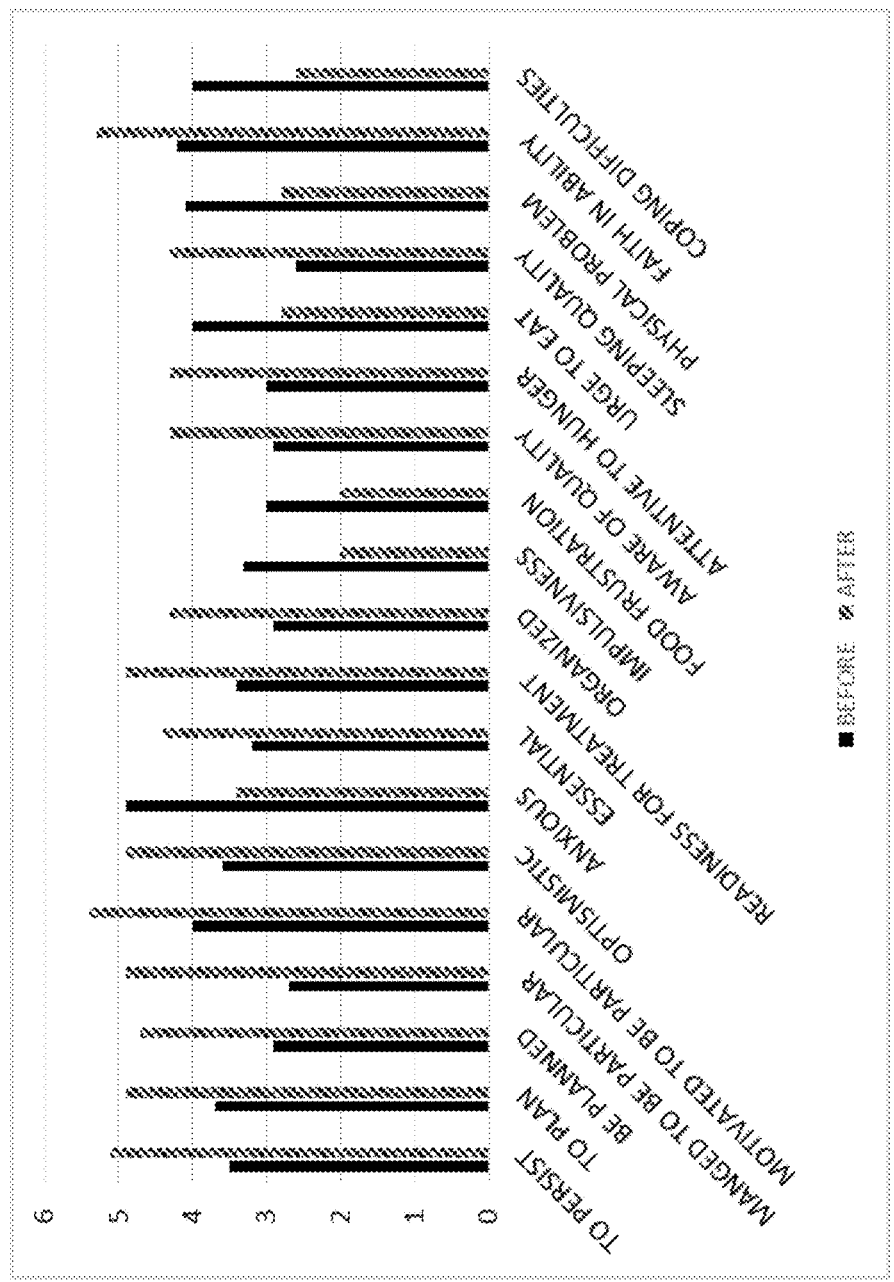
FIG. 16 Results of clinical study; perceptions and statements of the experimental group users, significant differences before versus after a series of neurofeedback training ($p<0.05$)
Figure 17:
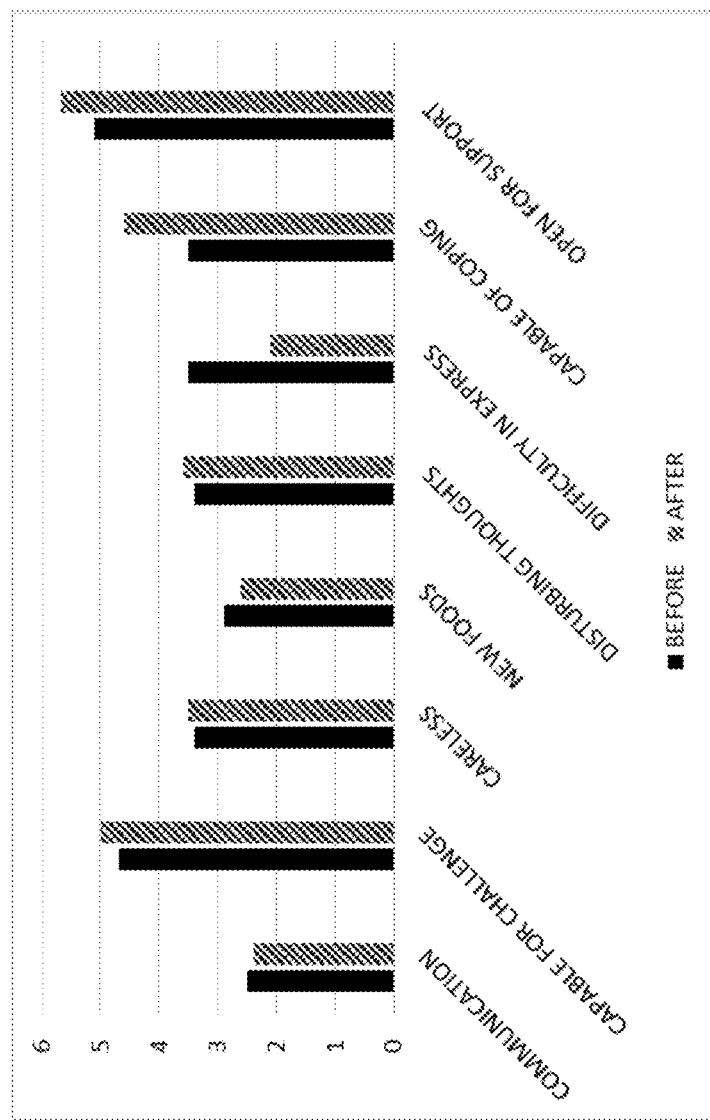
FIG. 17 Results of clinical study; perceptions and statements of the experimental group users, non-significant differences before versus after a series of neurofeedback training ($p>0.05$)

The participants in the experimental group felt that the ability to plan, plan, and succeed successfully in food planning was consistent with optimism, as shown in FIG. 16. However, in terms of support, communication, expression, there was no significant change in training, See FIG. 4. This is in line with the findings from family questionnaires, according to which the family does not expect a physiological improvement in the subjects, but rather reports an increase in their perception of the patient's level of optimism, dedication and perseverance. Test results for samples are paired in FIGS. 16 and 17.

3. Additional Physiological Indices:

Weight change In the t-test for independent samples, a significant difference was found between the control group and the experimental group in the mean weight change during the experimental period. As shown in Table 7, the average group of participants in the experimental group lost 2.25 kilograms during the experiment, while the control group gained an average weight of 0.4 kilograms.

TABLE 7

Weight changes during the experimental period

| | STATISTICAL TEST | CONTROL GROUP | STUDY GROUP |
|---|---|---|---|
| Average weight change during the experimental period | t(44) = 2.25 p < 0.05 | M = +0.4 SD = 3.82 | SD = 2.32.25 M = − |

There were significant differences in the perceptions and statements of relatives of the experimental group before versus after a series of neurofeedback training (p<0.05) (see FIG. 14). The main findings are: Increase in the ability to organize means, increase in persistence, increase in temptation resistance, increased in being devoted and increase in awareness of the need to change. A significant decrease was found in emotional eating as in being troubled by incompetence.

A larger number of significant differences in the perceptions in the perceptions and statements of participants of the experimental group, before versus after a series of neurofeedback training (p<0.05) (see FIG. 16).

The main findings are: a significant Increase was shown in the abilities to persist, to plan, to be planned, to be optimistic, to be essential, to be organized, to be aware of quality, and to be attentive to hunger. A significant increase was also revealed in managing to be particular, motivated to be particular, readiness for treatment, sleeping quality, and faith in own ability. A significant decrease was found in being anxious, in impulsiveness, in frustration of food, in urge to eat in physical problems, but also in coping difficulties.

Other health values as they appear in blood tests After the training, changes in blood test values resulting from the behavioral changes in the subjects in general and in dietary behavior in particular and even out of the definition of illness, such as diabetes and cardiovascular disease, can be identified.

Following Behavior modification, eating behavior is changed, in forms such as reduction of impulsivity, awareness to order and organization, reduction of cognitive load, obsessiveness, etc.

The result is also expressed in blood tests due to nutritional change

It can be seen that following the study, the following changes were observed

Summary of Medical Parameters Observed Through Blood Tests:

Following the training, changes in blood test values, resulting from the behavioral changes of the subjects in general, and of dietary behavior in particular are observed. Some subjects' illness markers, such as diabetes and cardiovascular disease, have improved to the extent of no longer categorized as having the particular illness.

An example of this is in form of particular subject, reporting change in behavior, improved control and resistance to temptations alongside improved planning capacity, reduced junk eating. For that subject the levels of A1c decreased from 6.1 to 5.9 and thus reduced her the risk of diabetes.

Four additional subjects reduction of about 10% of LDL values was observed, thereby reducing vascular disease.

Conclusions:
a. Three subjects were removed from the risk group of fasting diabetes
b. One subject triglyceride levels reduced by 10%
c. One abnormal value of cortisol was examined at the end of the study in one subject, and was referred to the endocrinologist for further investigation
d. Two subjects reduced 10% of general cholesterol
e. Four subjects reduced LDL by 10%
f. Eleven out of 12 subjects reduced waist size
g. Total averaged weight loss is 2.5 kg per subjects
h. The control group experienced an average weight gain of about 450 grams during the study period The study group consisted of a "hard" composition, with a high age in average, previous diet experience, some with history of gastric bypass surgery.

The significant change reported in eating behaviors results from reducing addictions, reducing anxiety, balancing, improving control and improving positive performance.

Example 4

One embodiment describes the current invention in the VR form

The application—before you enter HMD:
User Name Registration
Enter code: Enter a code that you received for a free coupon
Caption: "Please insert your mobile device into your virtual reality glasses"

Application Charging Screen

Opening Caption Screen:
Dear users, Thank you for investing your time and putting your health and wellness in first place. You are in a 360 degree environment. In a moment this black space will be replaced by a virtual space of Michal's living room. When that happens, take a moment to look around and relax and internalize. The spatial observation.

The entire experience will be activated by staring at a button shaped like this: X (design will be decided)

Each time you see an X-shaped button, you'll have to look at it to make the selection.

Figure 19A:
FIG. 19 Representation of VR (virtual reality) photos.
Figure 19B:
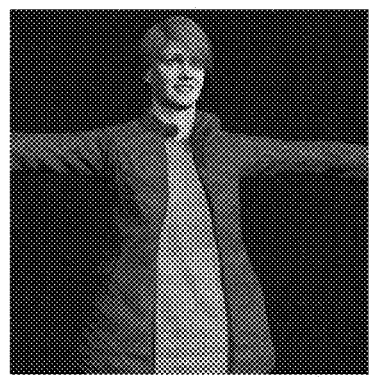

Taking a long look at the X is like making a choice.
To start, look at the X"
The user looks at the X
The space in now a living room (see FIG. 19A)
The User is asked:
Select: Are you:
Icon of a man/Icon of a woman
The user has to stare at the icon he chooses to "play".
After the selection—the virtual MICHAL (the inventor) enters the living room (see FIG. 19B)
MICHAL:
"Hello, come join me (Michal speaks male or female according to the user's choice—the text will be recorded in both versions).
Michal goes to the sofa and sits down, the user joins her and sits next to her (automatically happens)
I want to share with you my personal story, as you can see in the pictures here,
My whole life is struggling with obesity, and my best "successes" in dieting are weight gain.
I am a "mature" gastric bypass surgery in which I dropped 30 and gained 60 kg, Today, I am less than 40 kg of my peak weight but, most importantly, I managed to overcome the addictions which allows me to live a healthy lifestyle and completely avoid diabetes and cholesterol. About 12 years ago I felt that I was "getting off the cliff," every diet I did failed. I did not find a solution to my coping with eating.

The subject really frustrates me because every day I am a normal person: I am married, I have a child, a company owner from 2009, but in front of the food I fail, this will frustrate me very much. It was hard for me to accept that the addiction to chocolate, the urge to eat, the impulsiveness, and the difficulty in delaying gratification, such as aligning the cake, dominate me. Years of research have led me to understand that it has a name, management functions and part of attention deficit disorder.

From this pain I began to look for "training wheels". Hence the solution of a technology system submitted as a patent application in 2018 working on the brain waves training, from the understanding that everything is in mind! But needs some help.

This is a revolutionary technological product, the only one in the world that aims to characterize your personal challenge and give you a solution for relief. It is not another regular brain training or weight loss.

The end result—improvement until the disappearance of addictions, increasing control over food, while the "side effect" is weight loss.

Figure 19C:

Now, I'll walk you to Dr. Brain, but you'll go in alone."
Button:
"Continued"
(Appears frontally, the user must select it in order to switch to the clinic).
After the selection, space changes to the clinics
(On the shelves are pictures with professional credentials of the psychologist Dr. Brain) (see FIG. 19C).
Dr. Brain walks through the door.
Dr. Brain: "Welcome to the BOOST Institute, I am Dr. Brain, a senior researcher and lecturer in the field of psychology and counseling, I have specialized in brain training using technologies called neurofeedback, providing information on brain activity and training for optimal brain activity. I have treated hundreds of people over 15 years with great success and have written a book on neurofeedback therapy. Today, you will be diagnosed with an evaluation of the behavior of uncontrolled eating, which can rate the eating behaviors that affect your diet and characterize the problem In the brain, how? In charge of your eating behavior, and comparison of where his/her relation to the average population in your age group. This novel software will analyze your answers and you will be issued a protocol mental training tailored to you.

Today, medicine is progressing toward personalized medicine because it improves by 87% the success of the treatment. The differentiation of the diagnosis you will be doing right now is the ability to be precise and provide a therapeutic protocol in the field of eating behaviors and at the end you will receive a focused recommendation for the relevant brain area in the brain training session to improve control.

Dr. Brain: Now let's start the process. I will ask you questions and you will have to choose the answer that is most appropriate for you. When 1 indicates "not at all" and 6 indicates "very much", you must answer each question within 45 seconds. Dr. Bryn reads the 10 questions and also addresses the screen. (See inserting H in the attached document)

From the moment the question is finished, six numbers appear on the screen:

1 2 3 4 5 6 A timer countdown to 45 seconds To answer any question, this is the time the user must answer.

The Questionnaire:

https://drive.google.com/open?id=0B14YdZaBhzSYb-jBGQXkzVjclYk5LdVkwc3RSaWxGTm5mbWQ4

After diagnosis Dr. Brain turns to the user again.

Now let's move on to the second part, it's a little shorter and has a few repetitive questions. This section will tell you what your leading behaviors are, some are conscious and some are less.

In this section, questions will appear in Part B and again numbers will be graded.

After each answer, a response will appear for the user's choice for a few seconds and under the Continue button, if the user does not look at the button within 25 seconds, the questionnaire will automatically continue to the next question.

Magnificent! The system is currently weighing the data as soon as the data is ready.

After the user has finished answering all the questions Dr. Brain thanks him and tells him that immediately the results will appear on the screen which in the room.

On the screen, for example, you find that you are a frontal/temporal/perital type+percent+Explanation:

The frontal region—responsible for management functions—can explain uncontrolled behaviors associated with attention, planning and organization disorders, in making orderly and balanced decisions.

The parietal region—associated with resting the brain and emotional challenges such as anxiety or traumas—can explain emotional eating.

The right temporal region—which is responsible, among other things, for regulation, can explain eating that is not regulated in line with internal and external cues.

The frontal area—responsible for management functions—can explain uncontrolled eating behaviors associated with attention, planning, and organization disorders. It is known to "straighten the cake" or forgot to eat and when I get home, "I went down on the children's food and half the cold pizza."

The right temporal region, which is responsible for regulation, can explain eating that is not regulated in harmony with internal and external cues. Known as "snakes" that are never counted.

The parietal region, which is associated with brain resting and emotional challenges such as anxiety or traumas, can explain emotional eating, which is similar to a mobile phone loaded with video clips that requires complicated calculations. It is likely to be harder than a mobile phone whose memory is almost empty and available for downloading large applications. In dealing with addictions in eating, there is more stress on the system, the ability to resist addiction and temptations are weaker.

It was found that your eating behaviors at the level of (show a scale as in blood tests)

or

Norma: Your eating behavior conforms to the norm in the population, so continue! Improve and strengthen your eating behavior and improve your health with brain training tailored to you.

or

Just above norm: Your eating behavior has been found to deviate slightly from the norm in the population. Such behaviors have been shown in some studies to increase the potential for obesity, cardiovascular disease, and to reduce uncontrolled eating behavior, to achieve control and balance through customized brain training.

or

Above the norm: Your eating behavior has been found to exceed the norm in the population, but it is not terribly bad and there are things to do. Hundreds of people who have trained in exercise reported significant improvements in their quality of life, control, balance and reduction of addictions.

Caption:

Clinic: POWER BOOST

"The diagnosis is over. Thank you for putting yourself in first place

To purchase customized brain training, we give you a 50% credit for the amount of pay paid for the VR experience for brain training To redeem the benefit (valid for 60 days from the date of diagnosis) click here In addition, only for those purchasing the VR experience, personal diagnosis of eating behaviors for brain training+

You did not improve you did not pay!, Did not improve brain waves following brain training—your money will be returned 100% *

According to the regulations.

Logo and details: _____

Example 5

Case report 1: Dan, a 35 years old female is characterized by impulsive eating, but in the health promotion questionnaire it seems that "I do not sleep enough", "I have no satisfaction from work," "I'm not happy with my married life," and "suffer from chronic pain":

"I'm interested in starting cannabis treatment for pain relief."

The system will be characterized Dana by an impairment in the managerial functions—ambivalence. The system will identify the barriers to health promotion that cause Dana to cognitive overload (e.g., lack of sleep, marital distress, etc.).

The system recommends for Dana a suitable NF treatment: Dana is diagnosed with the therapeutic protocol of neurofeedback as having an impairment of management functions and therefore receives a tailored neurofeedback treatment.

Using the health promotion questionnaire, Dana was found to suffer from chronic pain that results in a cognitive load that affects a lot of preoccupation during the day and a little lack of attention to healthy eating organization processes.

Also, Dana is not satisfied with her marital relationship, which causes the emotional eating of comforting foods such as chocolate and ice cream, foods that lead to rapid sugar increases and increases the sense of low value and lack of control.

Through neurofeedback training to improve impulsivity, impulsive behaviors are expected to decrease in eating. Additionally, there will be an increase in personal referrals to create managerial priorities to create a healthy lifestyle rather than being swept away by the reality Case report 2: Uri, a 48 years old male, is characterized as having an addiction to work without obesity and food only in the evening is more than a predator in the evening that comes very hungry home and eat what is in the refrigerator including the leftovers of the children.

During the day, Uri eats cookies during the meetings and drinks coffee with sugar to overcome the fatigue. Thus, in the evening, Uri is very hungry and ate everything he could find, without the prior planning of a balanced and healthy meal.

By characterizing the promotion of health and personal characterization, Uri is characterized by eating habits as well as a personality type.

Uri is given a protocol of neurofeedback treatment. His Behavior is characterized by procrastination and impulsivity and is suitable for management dysfunction.

Neurofeedback training combined and personal guidance gives Uri the ability to route his diet better so that his habits are more orderly.

This way, Uri has more energy during the day, his medical condition improves, as well as the creation of preventive medicine for future diseases such as reducing diabetes and cardiovascular disease resulting from unbalanced eating.

Case report 3: Rami purchased a dog last year. Since then, rami walks with the dog every day, at 5:30. Therefore he walks five times more than the previous year. Additionally, during the day he does not eat commercial food but only home-cooked food.

You would expect him to lose weight. However, because of poor sleep quality (because of pressure at work) and shorter sleep hours, he gained weight. Furthermore, when he is tired he drinks sweetened drinks at work. He was found to have sleep apnea due to a polyp in his throat Using the current invention, improves his sleep quality, reduces his workload at work, as well as serving as adjunct treatment for sleep apnea, thus stops the weight gain.

Case report 4: John and Mila married couple about 4 years old and 30 years old fail to bring children, all physiological tests are normal. Both work and lead a normal life, do not smoke and exercise without obesity.

The couple came to a fertility clinic to find out why fertility was delayed without any physiological reason.

The questionnaire clearly has high levels of irritability in a word that suggests high levels of stress John has above-average anxiety levels due to uncertainty in his profession.

Neurofeedback training was offered to the couple according to a single treatment protocol in order to improve personal performance for everyone in general and to reduce anxiety to the word and anxiety for John.

Example 6

Experts declare the dry industrial food we buy for our pets is just as harmful to them as a regular diet of hamburger, pizza, and sweetened drinks will hurt us. They say that industrial food does not contain the necessary nutrients for a dog or cat.

That allergies and obesity reduce the longevity of dogs and cats who feed on industrial food. Eating unbalanced and nutritionally feeding animals can lead to a variety of unwanted behaviors. The current invention can be used to treat pets and assist in reducing overweight and treat eating disorders is pets or accompanying animals.

By characterizing animal behavior, using a questionnaire filled by the animal owner, and without a need for an EEG test, it is possible to identify the causes of abnormal behavior, and to improve the condition of the animal Example 7

Figure 4:
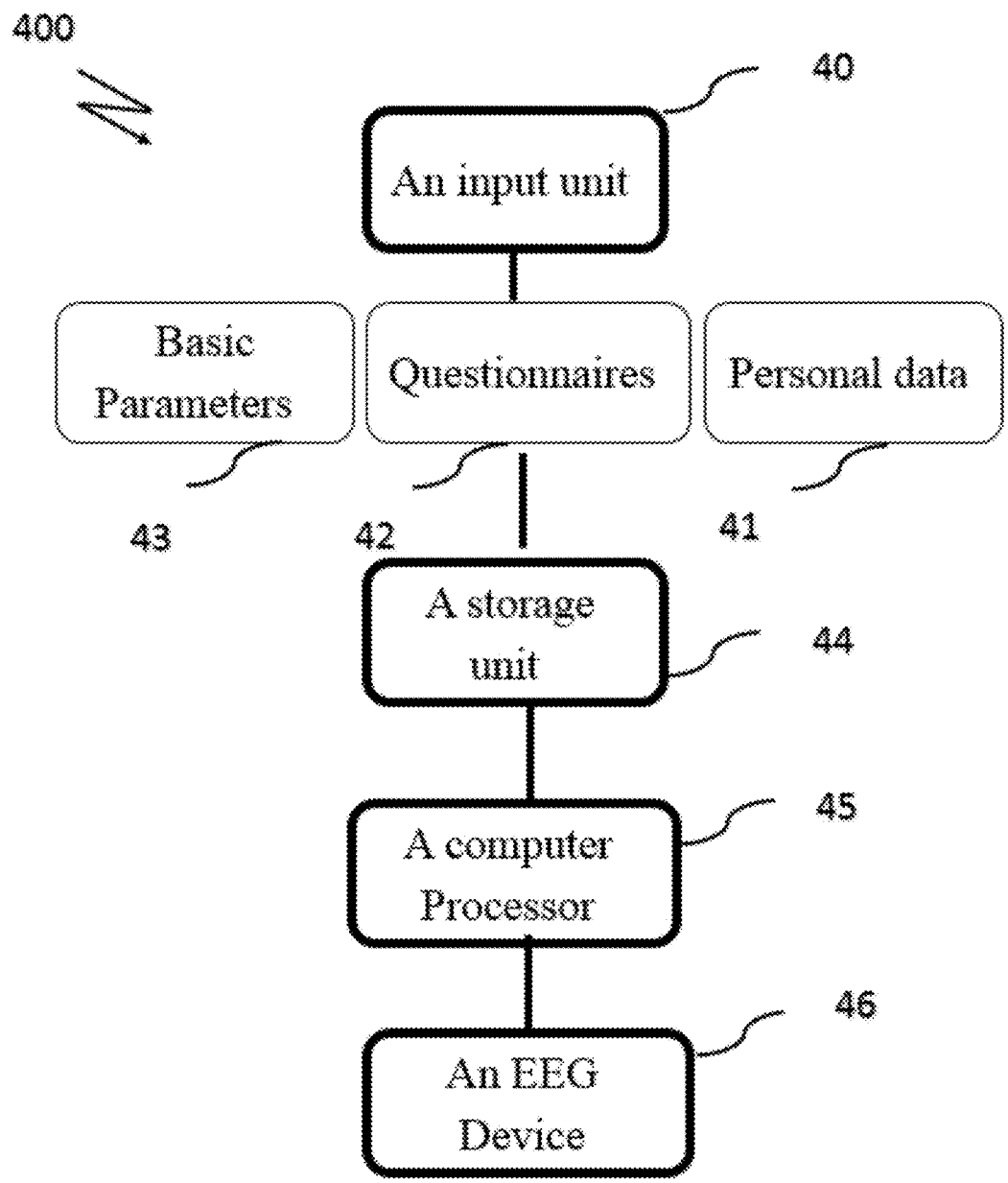
FIG. 4 A system for diagnosing and determining a treatment protocol for mammalian subject, according to the best mode embodiment of the invention.

The current invention is a neurofeedback computerized system and method for diagnosing and treating obesity, eating behavior/disorders and derived health conditions FIG. 4 is a block diagram of the best mode system. The system (400) comprises: an input unit (40), which receives personal information regarding the subject. This personal information includes: basic parameters (43) such as age, gender, weight and height, BMI, body fat, muscle mass and refers to basic input data (item 13 in FIG. 1) personal questionnaires (42) personal questionnaires are questionnaires for AD(H)D classification, with an emphasis on managerial functions including impulsivity, procrastination, ambition questionnaire, eating and activity and sleep habits questionnaire; health promoting questionnaire designed to diagnose health habits; or eating and diet preferences questionnaire etc. eating disorders un-controlled eating accompanying diseases, anxiety, addictions, pain, sexuality and fertility problems, fibromyalgia performance, sleep disorders, ADHD, ADD O.C.D or autism.

Active input data (item 14 in FIG. 1); personal physiological, social and behavioral data (41) collected continuously or time-lapsed of the subject by means of a wearable or a portable device. The physiological data include parameters such as: distance travelled by the subject, velocity, heart rate, blood pressure, body temperature and sleeping time. Social data includes parameters such as: duration of phone calls (minutes of speech/24 h), numbers of outgoing and incoming calls and text messages/24 h), identification of calls and callers, number of calls, length of calls, number of unique calls, text messages, and social networks' usage such as Facebook, LinkedIn, Twitter etc.; the behavioral data includes general activity related to nutrition such as visits in restaurants, in fast food sites, and activity related to training and exercising such visits in swimming pools, gym, etc. Refers to passive continuous input data (item 12 in FIG. 1). A web page or an application to capture all personal data, and data collected refers to a captive patient portal (CPP) (item 15 in FIG. 1). A storage unit (44) for storing all above personal data along with related data, refers to a data base (item 16 in FIG. 1). A computer processor (45 in FIG. 4; item 19 in FIG. 1) which uses specific algorithms to process above-mentioned personal data, and determines a treatment protocol (46 in FIG. 4; item 15 in FIG. 1). The treatment protocol contains personalized detailed instructions for neurofeedback training. An EEG device for neurofeedback training refers to EEG cap (item 20 in FIG. 1). This EEG device contains one EEG electrode located at the prefrontal cortex (PFC) area of the brain; and a second movable EEG electrode. The location of this second electrode is specifically determined by the personal treatment protocol. The system further uses the collected personal data in order to alert the subject when enters un-recommended sites such as fast food restaurants or praise the subject when exercises at the swimming pool or at the gym.

Example 8

Block chain is a system in which a record of digital transactions made are maintained across several computers that are linked in a peer-to-peer network. Blockchain technology guarantees greater transparency, security, and decentralization. The blockchain operates by spreading a continuous growing ledger of records, which are time stamped over a wide array of private computers across the world. This assures that the records cannot be altered, deleted or manipulated.

Figure 5:
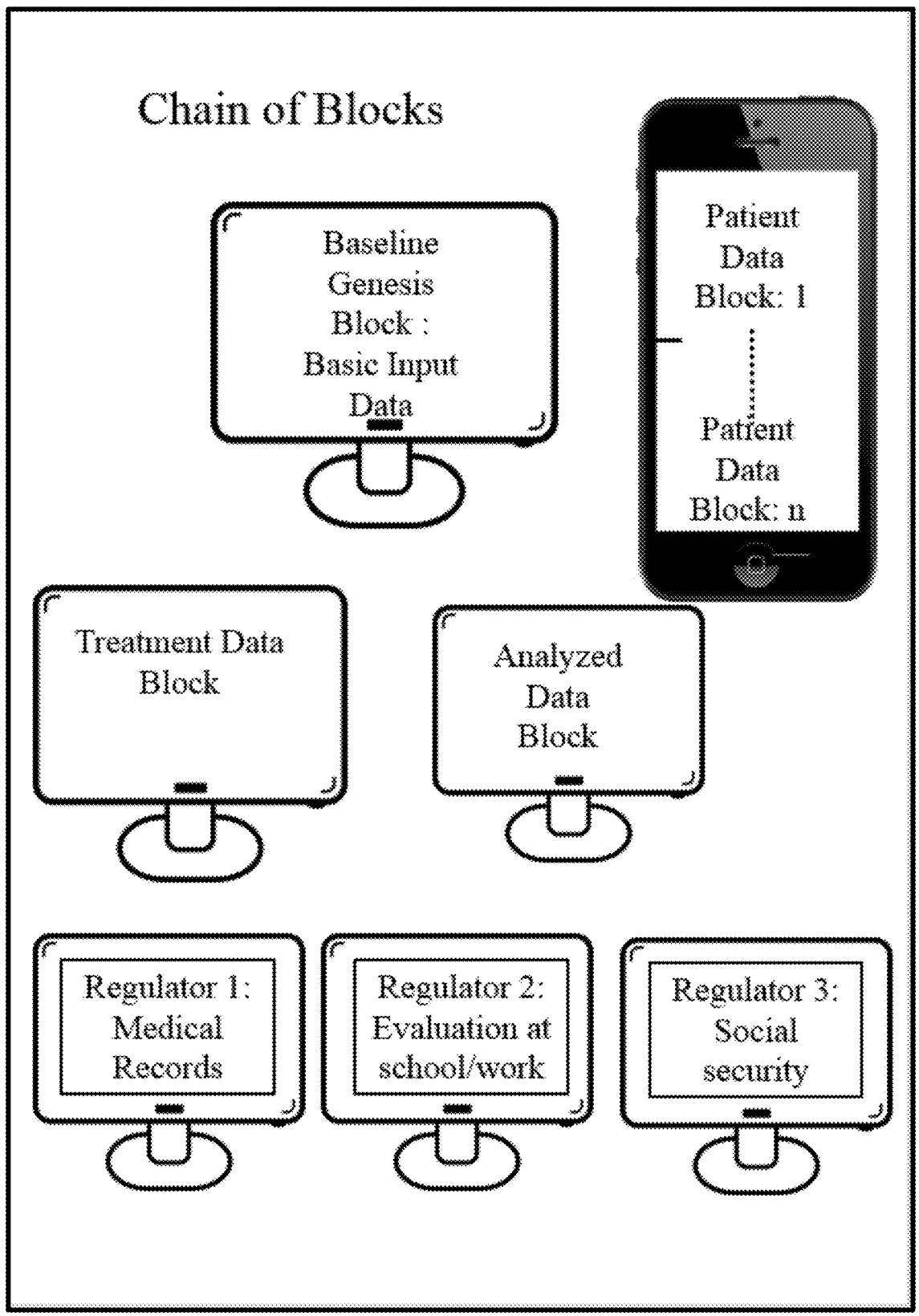
FIG. 5 A block chain illustration according to yet another embodiment of the invention.

Blockchain is designed specifically to accelerate and simplify the process of how transactions are recorded. This means that any type of asset can be transparently transacted using this completely decentralized system. The current invention is a system which is suitable also for block chain ledger. The block chain for the current invention is illustrated in FIG. 5.

Example 9

Machine learning can be described as software that changes when it learns from new information. As the software is self-adaptive, it is not necessary to add new rules manually. Deep learning is the most prospective area of machine learning. It is based on neural networks that require large data volumes to teach themselves.

The healthcare industry historically has generated large amounts of data, driven by record keeping, compliance & regulatory requirements, and patient care. While most data is stored in hard copy form, the current trend is toward rapid digitization of these large amounts of data. These massive quantities of data (known as 'healthcare big data') hold the promise of supporting a wide range of medical and healthcare functions, including among others clinical decision support, disease surveillance, and population health management The big data of the current invention is collected by comprises Basic Input Data Active Input Data and Passive Continuous Input Data, and is compared to data obtained for other users of the current invention, to data obtained for users of other systems and to any other data bases.

According to preferred embodiment, the current invention is a machine learning system, which studies the personal responses of the treated subject to the treatment protocol, to the alerts, recommendations etc., and accommodates the system to optimize that treatment and recommendations for the same treated subject.

Example 10

Figure 6A:
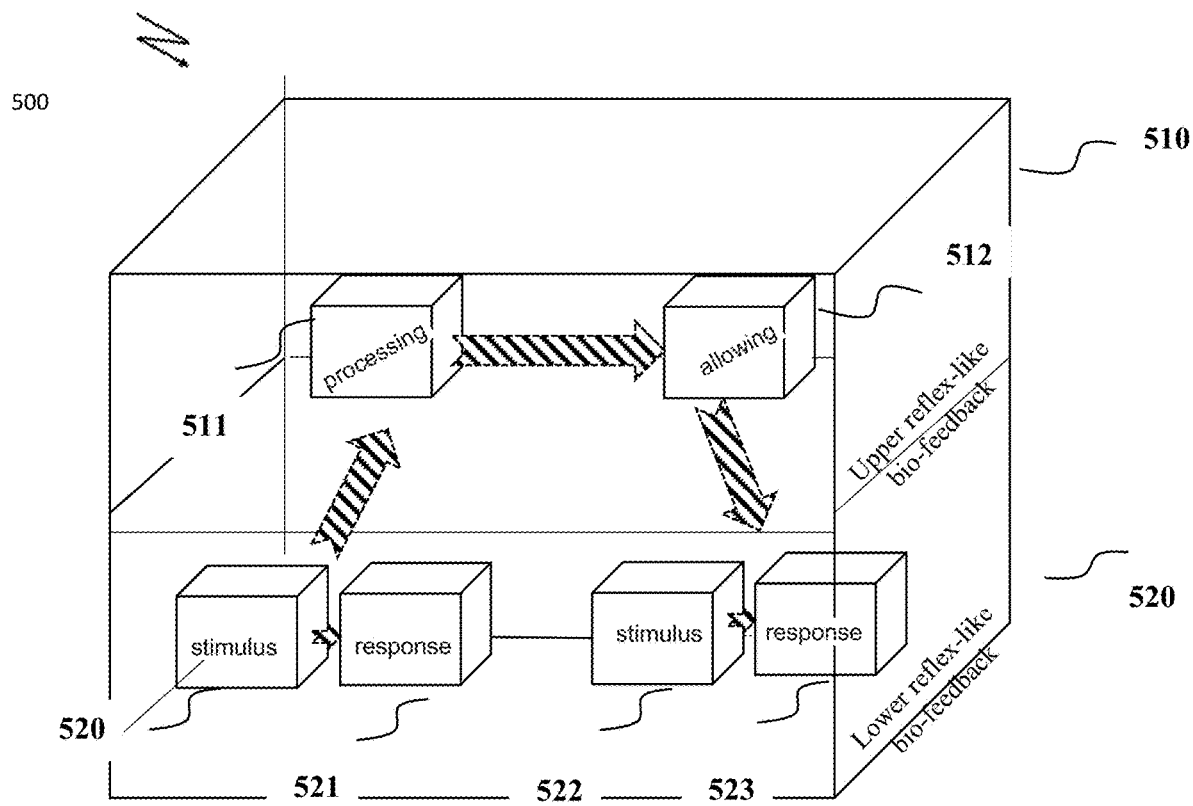
FIG. 6 A description of the biofeedback unit of the current invention.

FIG. 6 depicts the biofeedback module of the current invention. The biofeedback unit of the current invention (500) is composed of two sub-units: Lower reflex-like bio feedback sub-module (LRBL, 520), is a sub-unit responsible for responses (521 and 523) for all stimuli (520 and 522) provided by the mammals using the system. Upper reflex-like bio feedback sub-module (URLB, 510) is a sub-unit responsible for integrating the stimuli and the responses of the LRLB, as well as hierarchizing and prioritizing the stimuli response and selecting the most important response. (see FIG. 6 for the description of the biofeedback module and FIG. 7 for the biofeedback method and process). The LRBL (520) provides responses for any stimuli derived from mammalian users. Any applicable stimulus is followed by a response. For example: an example for a "bad" stimulus: visiting a gambling site, will result in a "punishment" by lowering "grades" or reducing deserts for the next meal; an example for a "good "stimulus: walking more than 30 min, will result in a "treat" by providing a friendly text message, or a coupon for buying a new pair of sport's shoes, etc.

Figure 6B:
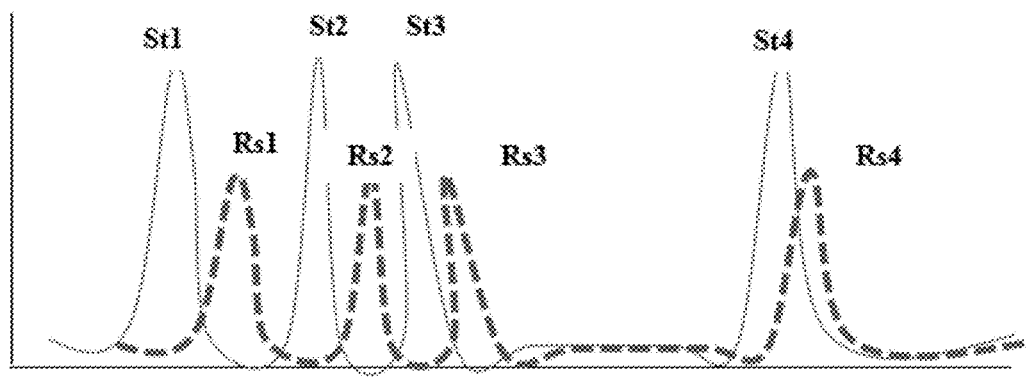
Figure 7:
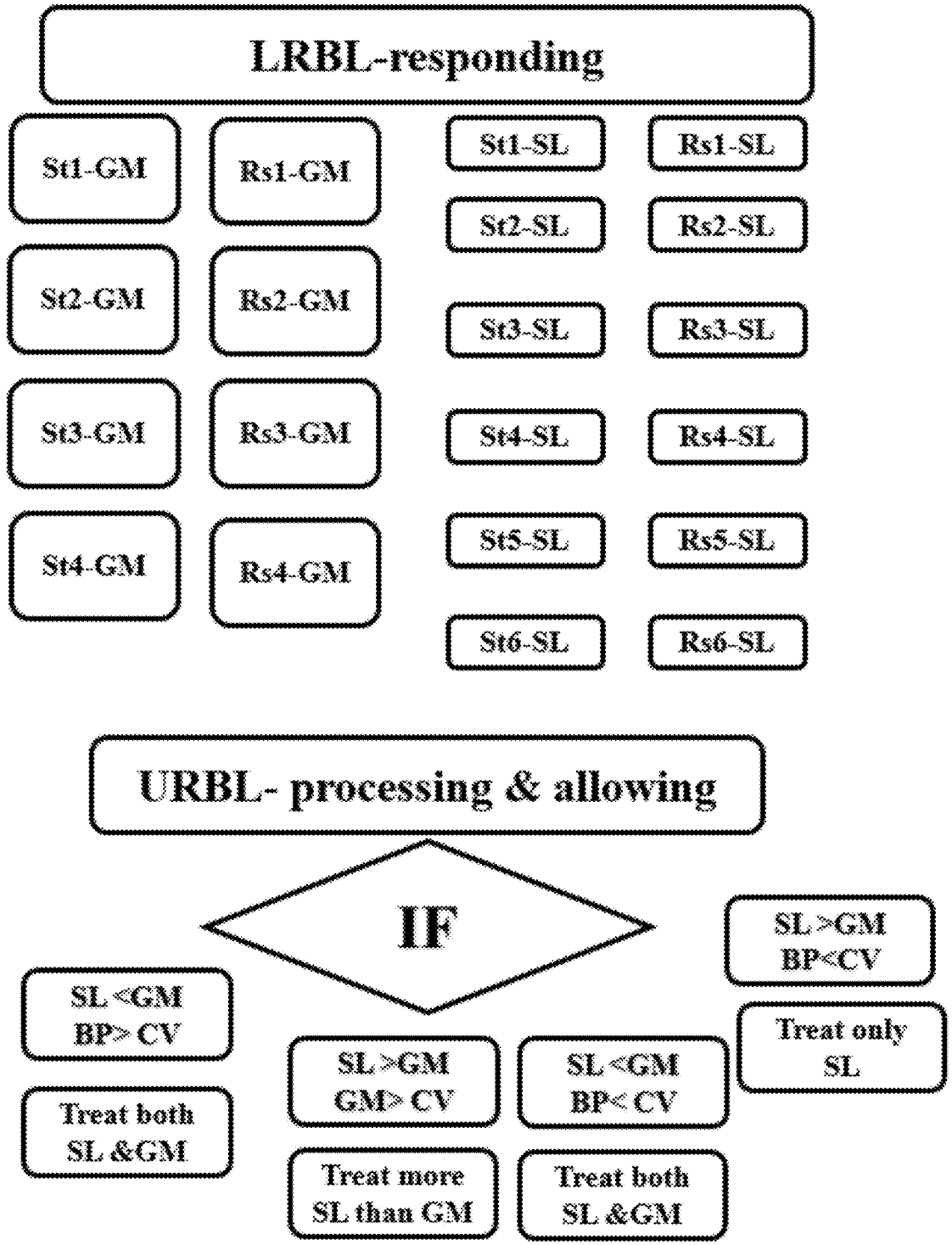
FIG. 7 A description of the biofeedback method of the current invention; GM—gambling; SL—Sleeping-less; NR—Normal range CV—Critical value; St—stimulus; Rs—response, BP—blood pressure.
Figure 8:
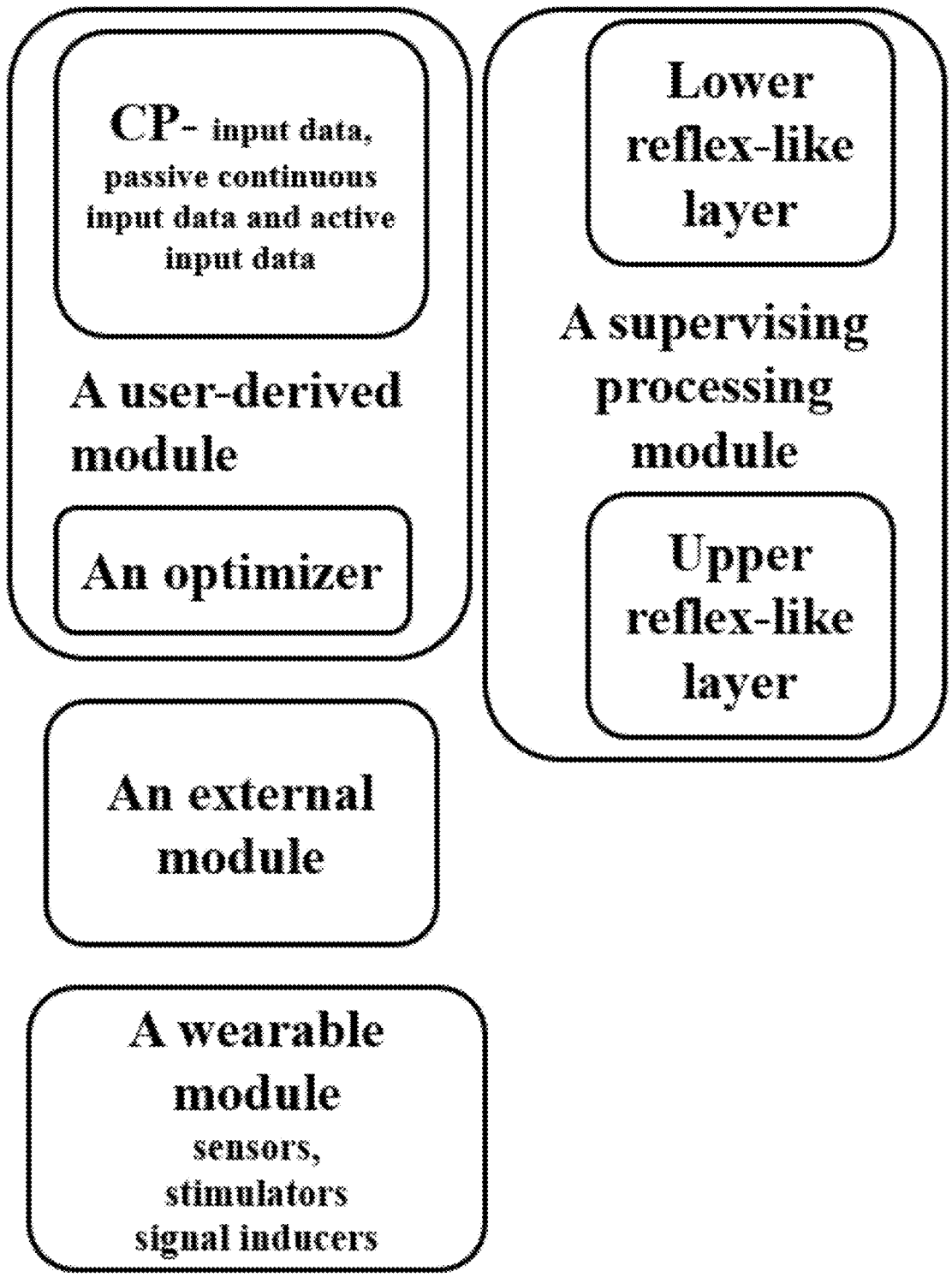
FIG. 8 A description of the biofeedback unit of the current invention; FF—fast food; SM-SL; CV—critical value; St—Stimulus; Rs—response.

Responding for every "bad" stimulus, will result in decreasing of the frequency of this type of stimulus, as depicted in FIG. 6B. St-Stimulus, Rs-Response. FIG. 7 depicts the process of bio-feedbacking. The stimuli examples depicted are gambling (GM) and sleeping-less (SL, sleeping less than 5 hours for an adult between ages 20-50). The URBL system will firstly prioritize all stimuli by their order of importance, magnitude, frequency, significance and relevance to overall well-being. Additionally, the URBL uses normal ranges (NR) and critical values (CV) of the mammalian user of the current invention. These normal ranges and critical values are related to the stimuli and comprise, inter alia, of quantitative measures of, for example, blood pressure, body mass index (BMI), EEG recordings, body temperature, etc.

According to the above, a non-limiting example is the stimulus of sleeping-less, which is more significant than the stimulus of gambling. Thus, when the system assess the SL events and of gambling events of a specific user, the URBL prioritizes the SL events. When a user has several events of GM stimuli (i.e. vising at fast food restaurants, St1-St4-GM) and several events of SL (St1-St6-SL), he/she receives response for each of this stimuli (Rs-GM for GM stimuli and RS-SL for SL stimuli), operated by LRBL sub-unit. The URBL system assesses these LRBL-operated sets of stimuli-responses. Since sleeping-less (SL) is set to be superior to gambling (GM) visits, then in the case SL event frequency is higher than GM event frequency, the URBL sub-unit ceases the LRBL-related response for GM and retains only the LRBL-related response for SL. This is true as long as GM visits are do not affect the related parameter, for example, blood pressure (BP). Nevertheless, in the case that BP value is higher than a critical value (CV); then the URBL sub-unit does not cease the LRBL-related response for GM and retains both the LRBL-related response for SL and the e LRBL-related response for GM.

In the case SL event frequency is lower than GM event frequency, and BP value is within its normal range; the URBL sub-unit continues both the LRBL-related response for SL and the LRBL-related response for GM (FIG. 7).

Example 11

Figure 9:
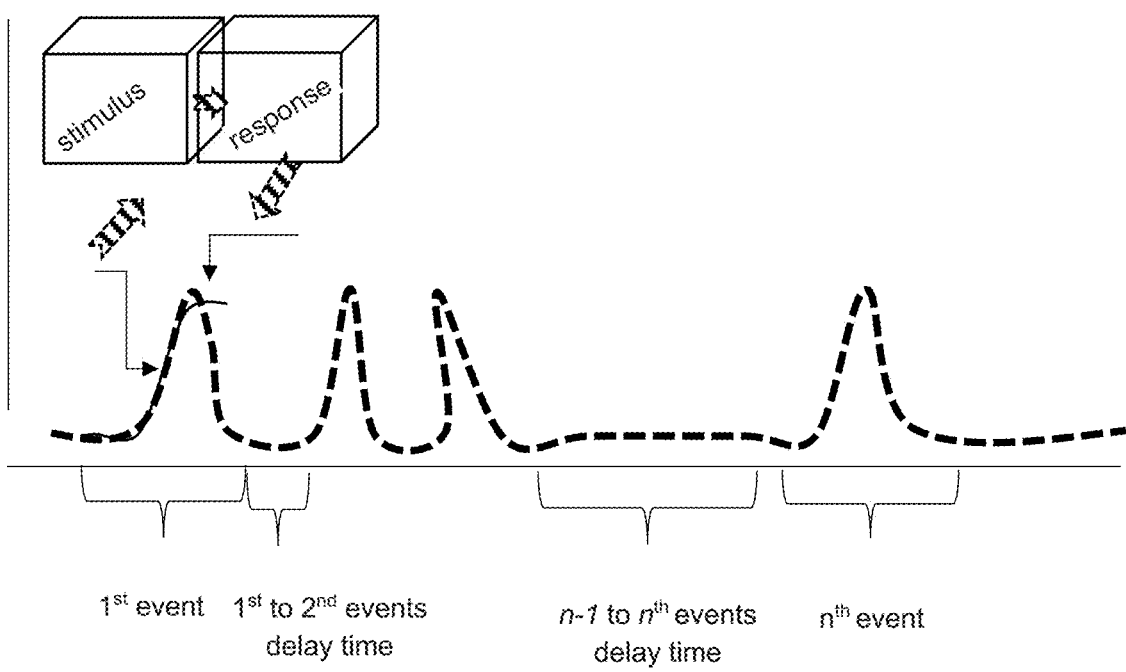
FIG. 9 A stimulus-response biofeedback method for $1^{st}$ and $2^{nd}$ events of the lower reflex-like bio-feedback of current invention.
Figure 10A:
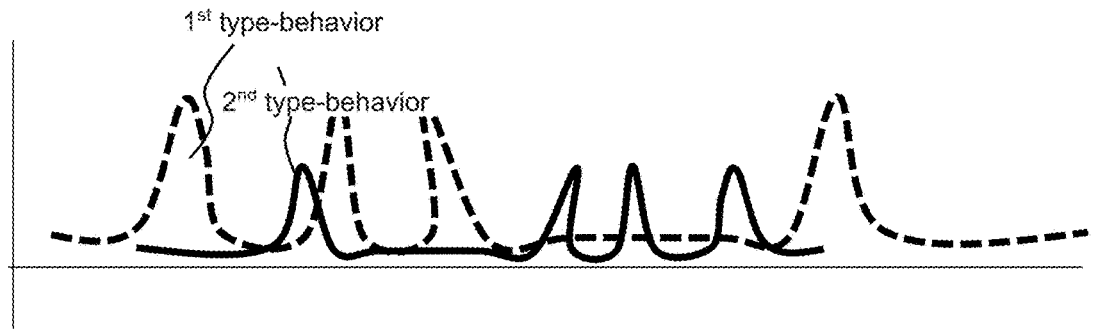
FIG. 10 A description of the function of the multilayered bio-feedbacking module of the current invention.
Figure 10B:
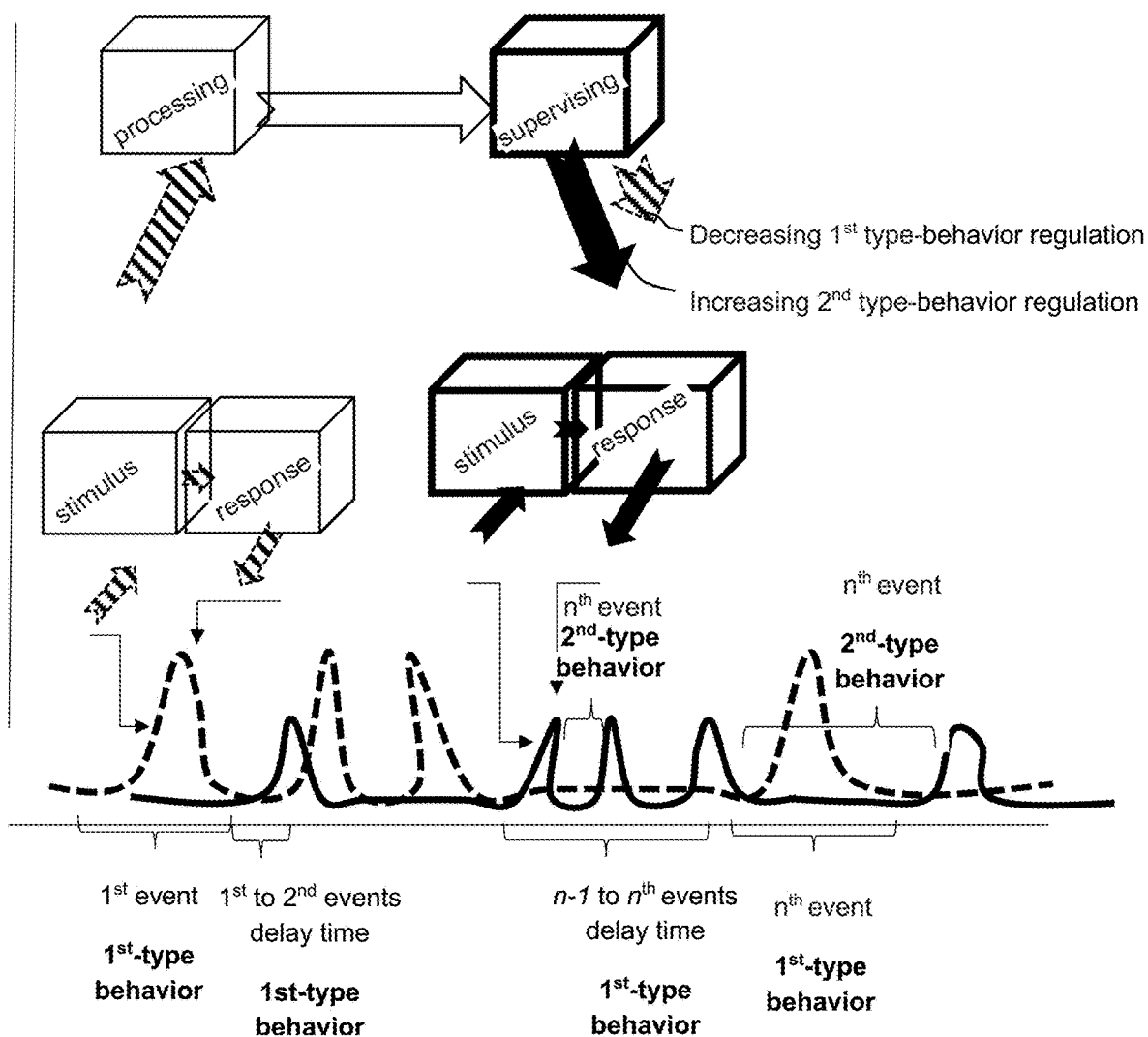
Figure 11:
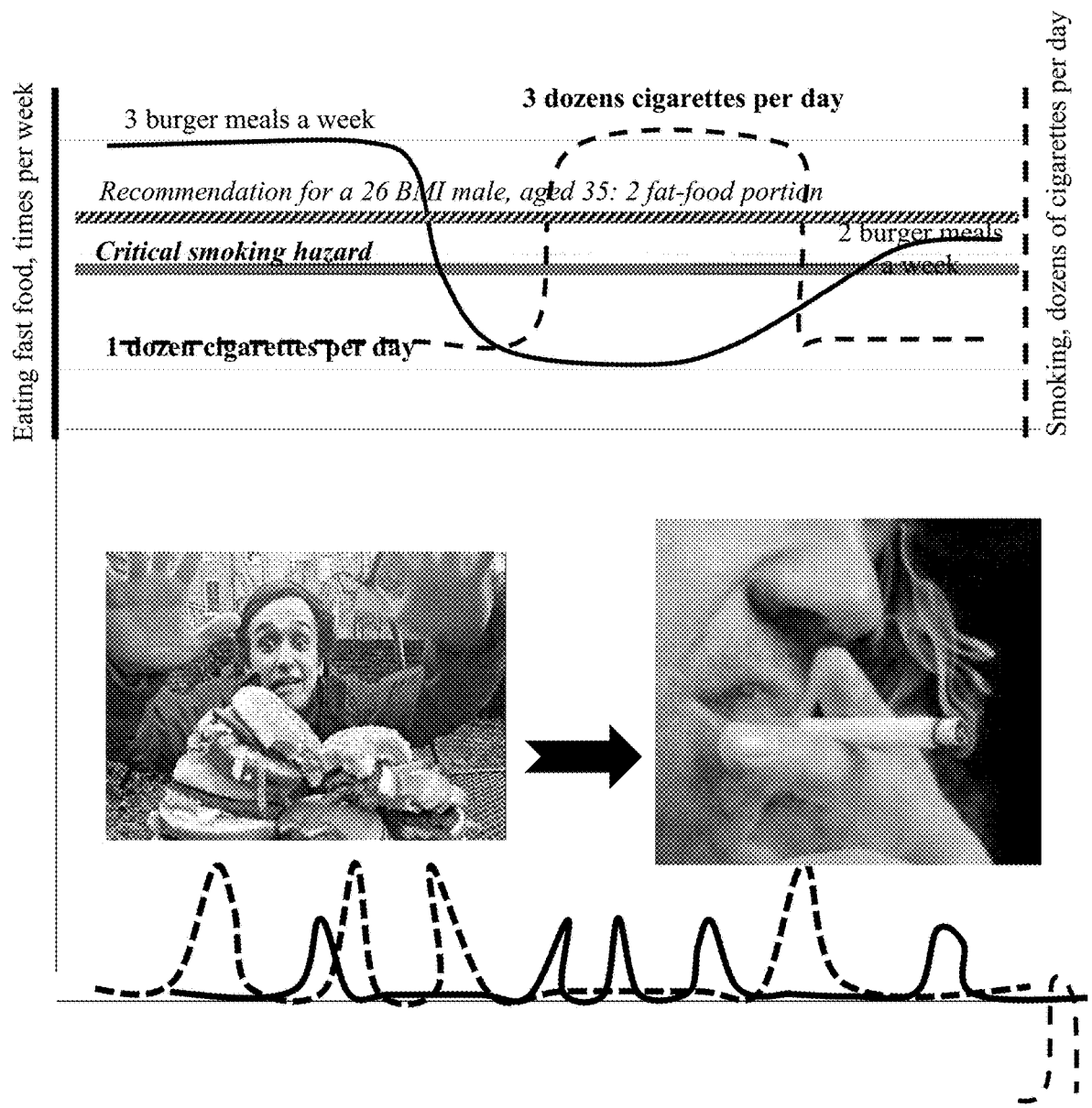
FIG. 11 A description of the combined function of the multilayered bio-feedbacking module and the behaviors-hierarchy optimizer of the current invention.

Additional example of the current invention is a multi-layered bio-feedbacking system, comprising a user-derived module, comprising a (internal-data source) captive portal data input (CP); the data is selected from a group consisting of input data, passive continuous input data and active input data; an external module comprising database derived from user's logged behavior; a wearable module, inter-communicable with the user derived module, comprising: at least one first sensor and at least one second sensor; the at least one first sensor is configured to log at least one first user's behavior, the at least one first behavior is characterized by a series of n events, n is an integer number being greater than or equals 1; and, the at least one second sensor is con Figured to log at least one second user's behavior, the at least one second behavior is characterized by a series of m events, m is an integer number being greater than or equals 1; and, at least one first and at least one second stimulation modules for stimulating a response for the at least one first and second user's behaviors, respectively, the response is stimulated in connection with the n' and m' events; n' and m', respectively, are an integer numbers, each of which is being greater than or equals 1; each of which of the at least one first and second stimulation modules are in connection with either or both; one or more signal inducers con Figured for a conscious alert; and one or more signal inducers con Figured for either a conscious or a subconscious stimulation at one or more locations of user's brain; a multilayered supervising processor structured with at least one first stimulus-respond lower reflex-like bio-feedback layer, and at least one second processing-supervising upper reflex-like bio-feedback layer; the processor comprises a user driven behaviors-hierarchy optimizer configuring for storing and processing parameters derived from user's behavior, weighing and defining hierarchy of the same, and either offline or online providing critical go/no-go values and allowable measures' range for the parameters; the processor is con Figured for operating as follows: in the lower reflex-like layer, and for both at least one first and at least one second behaviors, by means of at least a portion of the sensors intercommunicated with the wearable module, detecting the n and m events and defining the same as $n^{th}$ or $m^{th}$ stimulus; by communicating with the behaviors-hierarchy optimizer, correlating the stimulus with at least one parameter derived from user's at least one first behavior, weighting the parameter, and subsequently defining a response for the at least one first behavioral stimulus; in the upper reflex-like layer, and for both at least one first and at least one second behaviors, weighting the n and m events; detecting prevalence and magnitude of the events, processing the same, and supervising the lower reflex-like layer such that one of the following is being held true: decreasing response for stimuli of the first behavior if both hierarchy of second behavior is higher than hierarchy of first behavior prevalence and magnitude of the first behavior is lower than prevalence and magnitude of the second behavior; decreasing response for stimuli of the first behavior if both hierarchy of second behavior is higher than hierarchy of first behavior prevalence, magnitude of the first behavior is higher than prevalence and magnitude of the second behavior; and at least one parameter derived from user's first behavior is lower than critical go/no-go, and values of the at least one the pre-determined parameter are within allowable measures' range; allowing response for both stimuli of the of the first behavior and stimuli of the second behavior, if both hierarchy of second behavior is higher than hierarchy of first behavior, prevalence and magnitude of the first behavior is lower than prevalence and magnitude of the second behavior, and at least one parameter derived from user's first behavior is higher than critical go/no-go, and values of the at least one the pre-determined parameter are not within allowable measures' range; and allowing response for both stimuli of the of the first behavior and stimuli of the second behavior, if both hierarchy of second behavior is higher than hierarchy of first behavior, prevalence and magnitude of the first behavior is higher than prevalence and magnitude of the second behavior, and at least one parameter derived from user's first behavior is higher than critical go/no-go, and values of the at least one pre-determined parameter are not within allowable measures' range (see FIGS. 9-11).

FIG. 9 depicts graphic description of the function of lower reflex-like layer of the multilayered bio-feedbacking system of the current invention. This lower reflex-like layer detects a plurality of events. Of these events, the lower reflex-like layer detects a stimulus of a "bad" behavior, for example visiting a fast-food site. Following detection of this stimulus, the lower reflex-like layer responds by sending an alert for a "punishment" of this use: i.e. reducing amount of dessert for the next meal, lowering accumulated credits etc. In order to trach the user to avoid this "bad" behavior, the lower reflex-like layer responds for any event, resulting elongation of the delay time between the events.

FIG. 10 depicts graphic description of the combined function of upper and lower reflex-like layers of the multi-layered bio-feedbacking system of the current invention.

FIG. 10A depicts the graphic description of two sets of events: $1^{st}$ type behavior events (blue) and $2^{nd}$ type behavior events (red). For example $1^{st}$ type behavior is visiting at fast-food sites, while $2^{nd}$-type behavior is smoking cigarettes.

FIG. 10B depicts the combined functioning of upper and lower reflex-like layers of the multilayered bio-feedbacking system of the current invention in relation to $1^{st}$ type behavior and $2^{nd}$ type behaviors. As explained in FIG. 9, the lower reflex-like layer detects a stimulus of a "bad" behavior, for example visiting a fast-food site and responds, in order to lower its magnitude and frequency. The lower reflex-like layer detects additional stimulus of a "bad" behavior, for example smoking (red, $2^{nd}$-type behavior). The upper reflex-like layer is acting by processing the events' data as well as stimuli and response of the lower reflex-like layer and supervising the responses. The upper reflex-like layer, with the support of the user driven behaviors-hierarchy optimizer, prioritizes and determines the hierarchy of these two events. In this example, smoking behavior has a higher hierarchy than visiting fast-food sites. Thus, the upper reflex-like layer is acting by increasing the regulation regarding highly-prioritized behavior (2nd type behavior, i.e. smoking); while decreasing responses to $1^{st}$ type behavior, i.e. visiting fast-food sites.

This methodology of supervising the response and selecting the important behavior which deserves most of the responses, assists in treatment of the most important and crucial behaviors, and eliminates response on non-important events. This method also improves the overall compliance and commitment of the user to this life-style improving system.

FIG. 11 depicts another non-limiting example of the combined function of upper and lower reflex-like layers of the multilayered bio-feedbacking system of the current invention.

A user of the current system has two types of behavior: eating fast foods i.e. burger meals (blue, $1^{st}$ type behavior) and smoking cigarettes (red, $2^{nd}$ type behavior). Supervising of these behaviors is performed by increasing regulation of one type of behavior, once this type of behavior is highly prioritized (for example smoking has a higher hierarchy over fast-food eating) or a user-parameter derived from this behavior is not within allowable measures, (i.e. critical smoking hazard), or both.

Example 12

John, a 30-year-old man, has been working for many hours and does not eat properly. John applied for weight loss training: John first manually fulfilled the questionnaire to determine the treatment protocol, and then the treatment protocol was determined.

At the same time, John fills out the health promotion questionnaire manually and also wears the biometric watch/bracelet that began collecting data.

It appears that John's self-reported data are partial and that the information obtained from the biometric watch/bracelet suggests that the reasons for uncontrolled eating of John, are not only due to the reasons he cited, but because of other reasons such as lack of sleep, poor quality sleep, and constant pain.

Therefore, the system will be directed to the continuation of designated neurofeedback treatments for symptomatic relief, and only after reaching a Quality Score lower than the initial weighted Quality Score, John will begin receiving references to more challenging recommendations that combine neurofeedback training:
  a. a location-based warning such as—please go to the park nearest you, where you can walk in and improve the amount of daily walking.
  b. another location-based warning—when John comes to a restaurant, he receives a warning about an informed choice of food c. early warning about sleeping, 3 hours prior to creating a quality sleep.

The invention claimed is:

1. A QEEG-based bio-feedbacking system characterized by
   a. a user-derived, internal-data source, captive portal data input (CP) having internal-data; said internal-data is selected from a group consisting of data comprising basic input data, passive continuous input data and active input data;
   b. an external-data source database;
   c. a graphical user interface (GUI);
   d. a QEEG wearable device configured for both sensing and for training a defined area of a patient's brain; and
   e. a computer processing manager (CPM) for processing both said internal-data and external-data, interconnected with said CP, said database and said GUI; said CPM is configured to instruct QEEG electrode mediated bio-feedbacking to train said defined area of the patient's brain according to a patient-data driven training-protocol.

2. The system of claim 1, wherein said system is useful for a treatment or an adjunctive therapy for at least one of therapies for eating disorders, uncontrolled or unbalanced eating, diabetes, sleep disorders, sleep apnea, uncontrolled behaviors, obesity, ADHD, addictions, ADD, eating behaviors, depression, anxiety, autism, anxiety addictions, pain, sexuality and fertility, fibromyalgia performance, emotional eating, impulsiveness, frustration of food, urge to eat, physical problems, and any combination thereof.

3. The system of claim 2, wherein said system is further configured to repeat collecting said internal data and said external data following said bio-feedbacking at a plurality of time points, to determine whether the patient is responsive; and to recommend the training to be continued if the patient is responsive, or to be discontinued if the patient is non responsive.

4. The system of claim 2, wherein said CP is further configured to collect said internal-data and said external-data following said treatment of said eating disorders, at n time points, wherein n is an integer equal or higher than 2, comprising of a first time point before start of said treatment of said eating disorders and a second time point at a later time over the life of said patient; further wherein said CPM is configured to provide instructions for 1 electrode mediated training to said defined area according to said patient-data driven training protocol, and said training is be continued, if a value of said patient's weight in said basic input data at second time point is lower than a value at said first time point.

5. The system of claim 1, wherein said captive portal data input (CP) is configured to collect and store said internal-data and external-data of said patient.

6. The system of claim 1, wherein said system is either stationary or mobile.

7. The system of claim 1, wherein said CPM comprises an algorithm configured to weigh results of said internal-data, with said external-data.

8. The system of claim 1, wherein said QEEG-based bio-feedbacking system comprises at least one of the group consisting of a wearable neurofeedback (NF) system and a wearable neurofeedback system using virtual reality (VR).

9. The system of claim 8, wherein said system comprises at least one QEEG electrode configured to train at least one brain area.

10. The system of claim 1, wherein said system is useful for increasing at least one selected from the group consisting of ability to organize, persistence, temptation resistance, devoting, awareness of a need to change, abilities to persist, planning, optimism, being essential, being organized, being aware of quality, being attentive to hunger, managing to be particular, motivating to be particular, readiness for treatment, sleeping quality, faith in own ability, and any combination thereof.

11. The system of claim 1, wherein said eating disorders are selected from a group consisting non-diagnosed eating disorders, unbalanced eating, uncontrolled eating, obesity, anorexia nervosa, bulimia nervosa, muscle dysmorphia, binge eating disorder (BED), other specified feeding or eating disorder, atypical anorexia nervosa, atypical bulimia nervosa, western industrial eating, orthorexia, excessive exercise, and any combination thereof.

12. The system of claim 1, wherein the patient is selected from the group consisting of patients not diagnosed with obesity, patients diagnosed with obesity, patients diagnosed with AD(H)D, patients not diagnosed with AD(H)D, patients diagnosed with eating disorders, patients not diagnosed with eating disorders, and any combination thereof.

13. The CPM of claim 1, wherein said CPM further provides instructions for cannabinoid-based therapy adjunct to said QEEG electrode mediated bio-feedbacking.

14. The system of claim 1, wherein said passive continuous input data comprises at least one of said patient's parameters selected from EEG, distance travelled, velocity, heart rate, blood pressure, body temperature, sleeping time, duration of phone calls, number of outgoing and incoming calls and text messages, identification of phone calls and callers, length of calls, WhatsApp messages, social networks' usage, visits in restaurants, visits in fast food sites, visits in swimming pools, visits in gym, camera photos, location, acquisitions and any combination thereof.

15. The system of claim 1, wherein said passive continuous input data is assembled by a device selected from a group of an EEG device, a camera, a mobile phone, a smartphone, a watch, a smart watch, a bracelet, a smart bracelet, a wristband, a smart wristband, a smart band and any combination thereof.

16. The system of claim 1, wherein said basic input data comprises personal details, said personal details are weight, body fat, height, age, BMI, muscle mass and gender.

17. The system of any of claim 1, wherein said active input data comprises at least one of a personal characterization questionnaire, an eating and diet preferences questionnaire, a "health promoting questionnaire" and any combination thereof.

18. A method of treating at least one of eating disorders, obesity, uncontrolled or unbalanced eating, diabetes, sleep disorders, sleep apnea and uncontrolled behaviors, the method characterized by:
   a. providing a user-derived, internal-data source and captive portal data input (CP) having internal-data; said internal-data is selected from a group consisting of data comprising basic input data, passive continuous input data and active input data;
   b. providing an external-data source database;
   c. providing a graphical user interface (GUI);
   d. providing an EEG wearable device configured for both sensing and for training a defined area of a patient's brain; and
   e. providing a computer processing manager (CPM) for processing both said internal-data and said external-data, interconnected with said CP, said database and said GUI; said CPM is configured to instruct electrode mediated bio-feedbacking to train said defined area of the patient's brain according to a patient-data driven training-protocol.

19. A method for rapid diagnosis of a patient, said method comprising:
- a. providing a user derived module, comprising an internal-data source and a captive portal data input (CP) having internal-data; said internal data comprises basic input data, algorithm-based questionnaires; and measurements of EEG;
- b. providing an EEG wearable device configured for both sensing and for training a defined area of patient's brain;
- c. providing an external-data source database;
- d. providing a graphical user interface (GUI); and
- e. providing a computer processing manager (CPM) for processing both said internal-data and external-data, interconnected with said CP, said database and said GUI; said CPM is configured to instruct electrode mediated bio-feedbacking to train said defined area of the patient's brain according to a patient-data driven training-protocol.

* * * * *